United States Patent
Kimball et al.

(10) Patent No.: US 9,526,921 B2
(45) Date of Patent: Dec. 27, 2016

(54) USER FEEDBACK THROUGH END EFFECTOR OF SURGICAL INSTRUMENT

(75) Inventors: Cory G. Kimball, Cincinnati, OH (US); Daniel W. Price, Loveland, OH (US); Geoffrey S. Strobl, Williamsburg, OH (US)

(73) Assignee: Ethicon Endo-Surgery, LLC, Guaynabo, PR (US)

( * ) Notice: Subject to any disclaimer, the term of this patent is extended or adjusted under 35 U.S.C. 154(b) by 0 days.

(21) Appl. No.: 13/276,673

(22) Filed: Oct. 19, 2011

(65) Prior Publication Data

US 2012/0116267 A1    May 10, 2012

Related U.S. Application Data

(60) Provisional application No. 61/410,603, filed on Nov. 5, 2010, provisional application No. 61/487,846, filed on May 19, 2011.

(51) Int. Cl.
*A61B 17/32* (2006.01)
*A61N 7/00* (2006.01)
(Continued)

(52) U.S. Cl.
CPC ........... *A61N 7/00* (2013.01); *A61B 17/00234* (2013.01); *A61B 17/2812* (2013.01);
(Continued)

(58) Field of Classification Search
CPC ........... A61B 19/54; A61B 201/00734; A61B 17/07207; A61B 2017/00398; A61B 2019/448; A61B 18/1442; A61B 17/2812; A61B 18/1445; A61B 18/12; A61B 18/00; A61B 17/320092; A61B 17/00234; A61B 18/14; A61B 17/320068; A61B 18/04; A61B 2018/0019; A61B 17/064; A61B 2019/4868; A61B 19/38; A61B 2017/2931; A61B 2017/0046; A61B 2019/4873; A61B 2018/00791; A61B 2018/1412; A61B 2018/1226; A61B 17/285; A61B 2017/00477; A61B 2019/4815; A61B 2017/293; A61B 2017/2929; A61B 2018/1455; A61B 2018/00988; A61B 2017/2933; A61B 18/1233; A61B 2018/00178; A61B 2017/00473; A61B 2017/00084; A61B 2017/294; A61B 2017/291; H02J 7/0045; Y10T 29/53913; Y10T 29/49895; Y10T 29/49005; H01M 2/10; H01M 2/26
(Continued)

(56) References Cited

U.S. PATENT DOCUMENTS 1,754,806 A    4/1930    Stevenson
3,297,192 A    1/1967    Swett
(Continued)

FOREIGN PATENT DOCUMENTS

CN    101819334    4/2013
DE    102008051866    10/2010
(Continued)

OTHER PUBLICATIONS

International Search Report and Written Opinion dated Jan. 26, 2012 for Application No. PCT/US2011/059212.
(Continued)

*Primary Examiner* — Sanjay Cattungal
(74) *Attorney, Agent, or Firm* — Frost Brown Todd LLC

(57) ABSTRACT

A surgical instrument includes a handle assembly and a transmission assembly including an end effector. The end effector includes a visual indicator, such as dots disposed on a clamp arm, to emit light from at least one LED disposed between the clamp arm and a clamp pad. The LED is
(Continued)

connectable to a power source. An outer sheath of the end effector is extruded to include a first set of electrical conduits. A distal assembly of the end effector includes the clamp arm, clamp pad, LED, and a second set of electrical conduits to mate with the first set of electrical conduits when the distal assembly is snap-fit into the extruded outer sheath. An ultrasonic surgical instrument includes an outer sheath configured to transmit light from an internally housed LED along portions of the outer sheath.

15 Claims, 11 Drawing Sheets

(51) Int. Cl.
    *A61B 17/00*     (2006.01)
    *A61B 18/00*     (2006.01)
    *A61B 18/04*     (2006.01)
    *A61B 18/14*     (2006.01)
    *H02J 7/00*     (2006.01)
    *A61B 17/28*     (2006.01)
    *H01M 2/26*     (2006.01)
    *H01M 2/10*     (2006.01)
    *A61B 18/12*     (2006.01)
    *A61B 17/064*     (2006.01)
    *A61B 17/285*     (2006.01)
    *A61B 17/29*     (2006.01)

(52) U.S. Cl.
    CPC ............... *A61B 17/320068* (2013.01); *A61B 17/320092* (2013.01); *A61B 18/00* (2013.01); *A61B 18/04* (2013.01); *A61B 18/12* (2013.01); *A61B 18/14* (2013.01); *A61B 18/1442* (2013.01); *A61B 18/1445* (2013.01); *H02J 7/0045* (2013.01); *A61B 17/064* (2013.01); *A61B 17/285* (2013.01); *A61B 18/1206* (2013.01); *A61B 18/1233* (2013.01); *A61B 34/25* (2016.02); *A61B 90/40* (2016.02); *A61B 2017/0046* (2013.01); *A61B 2017/0084* (2013.01); *A61B 2017/00398* (2013.01); *A61B 2017/00473* (2013.01); *A61B 2017/00477* (2013.01); *A61B 2017/00482* (2013.01); *A61B 2017/00734* (2013.01); *A61B 2017/291* (2013.01); *A61B 2017/293* (2013.01); *A61B 2017/294* (2013.01); *A61B 2017/2929* (2013.01); *A61B 2017/2931* (2013.01); *A61B 2017/2933* (2013.01); *A61B 2018/0019* (2013.01); *A61B 2018/00178* (2013.01); *A61B 2018/00791* (2013.01); *A61B 2018/00988* (2013.01); *A61B 2018/1226* (2013.01); *A61B 2018/1412* (2013.01); *A61B 2018/1455* (2013.01); *A61B 2090/0803* (2016.02); *A61B 2090/0813* (2016.02); *A61B 2090/0814* (2016.02); *H01M 2/10* (2013.01); *H01M 2/26* (2013.01); *Y10T 29/49005* (2015.01); *Y10T 29/49895* (2015.01); *Y10T 29/53913* (2015.01)

(58) Field of Classification Search
    USPC ............. 600/437–469; 601/1–3; 606/45–52, 606/160–169
    See application file for complete search history.

(56) References Cited

U.S. PATENT DOCUMENTS

| | | |
|---|---|---|
| 3,419,198 A | 12/1968 | Pettersen |
| 3,619,671 A | 11/1971 | Shoh |
| 4,034,762 A | 7/1977 | Cosens et al. |
| 4,057,220 A | 11/1977 | Kudlacek |
| 4,535,773 A | 8/1985 | Yoon |
| 4,641,076 A | 2/1987 | Linden et al. |
| 4,662,068 A | 5/1987 | Polonsky |
| 4,666,037 A | 5/1987 | Weissman |
| 4,717,018 A | 1/1988 | Sacherer et al. |
| 4,717,050 A | 1/1988 | Wright |
| 4,721,097 A | 1/1988 | D'Amelio |
| 4,768,969 A | 9/1988 | Bauer et al. |
| 4,800,878 A | 1/1989 | Cartmell |
| 4,844,259 A | 7/1989 | Glowczewskie, Jr. |
| 4,878,493 A * | 11/1989 | Pasternak .............. A61B 18/12 219/234 |
| 5,071,417 A | 12/1991 | Sinofsky |
| 5,107,155 A | 4/1992 | Yamaguchi |
| 5,144,771 A | 9/1992 | Miwa |
| 5,169,733 A | 12/1992 | Savovic et al. |
| 5,176,677 A | 1/1993 | Wuchinich |
| 5,246,109 A | 9/1993 | Markle et al. |
| 5,273,177 A | 12/1993 | Campbell |
| 5,277,694 A | 1/1994 | Leysieffer et al. |
| 5,308,358 A | 5/1994 | Bond et al. |
| 5,322,055 A | 6/1994 | Davison |
| 5,339,799 A | 8/1994 | Kami et al. |
| 5,358,508 A | 10/1994 | Cobb et al. |
| 5,361,902 A | 11/1994 | Abidin et al. |
| 5,429,229 A | 7/1995 | Chester et al. |
| 5,449,370 A | 9/1995 | Vaitekunas |
| 5,454,378 A | 10/1995 | Palmer et al. |
| 5,501,607 A | 3/1996 | Yoshioka et al. |
| 5,507,297 A | 4/1996 | Slater et al. |
| 5,561,881 A | 10/1996 | Klinger et al. |
| 5,578,052 A | 11/1996 | Koros et al. |
| 5,580,258 A | 12/1996 | Wakata |
| 5,582,617 A | 12/1996 | Klieman et al. |
| 5,590,778 A | 1/1997 | Dutchik |
| 5,592,065 A | 1/1997 | Oglesbee et al. |
| 5,599,350 A | 2/1997 | Schulze et al. |
| 5,630,420 A | 5/1997 | Vaitekunas |
| 5,630,456 A | 5/1997 | Hugo et al. |
| 5,690,222 A | 11/1997 | Peters |
| 5,741,305 A | 4/1998 | Vincent et al. |
| 5,776,155 A | 7/1998 | Beaupre et al. |
| 5,800,336 A | 9/1998 | Ball et al. |
| 5,817,128 A | 10/1998 | Storz |
| 5,868,244 A | 2/1999 | Ivanov et al. |
| 5,873,873 A | 2/1999 | Smith et al. |
| 5,882,310 A | 3/1999 | Marian, Jr. |
| 5,935,144 A | 8/1999 | Estabrook |
| 5,938,633 A | 8/1999 | Beaupre |
| 5,944,737 A | 8/1999 | Tsonton et al. |
| 5,951,575 A | 9/1999 | Bolduc et al. |
| 5,980,510 A | 11/1999 | Tsonton et al. |
| 5,997,531 A * | 12/1999 | Loeb ..................... A61B 18/24 606/13 |
| 6,018,227 A | 1/2000 | Kumar et al. |
| 6,051,010 A | 4/2000 | Dimatteo et al. |
| 6,056,735 A | 5/2000 | Okada et al. |
| 6,063,098 A | 5/2000 | Houser et al. |
| 6,066,151 A * | 5/2000 | Miyawaki ...... A61B 17/320068 606/169 |
| 6,083,191 A | 7/2000 | Rose |
| 6,099,537 A * | 8/2000 | Sugai ................. A61B 17/0684 606/143 |
| 6,165,191 A | 12/2000 | Shibata et al. |
| 6,204,592 B1 | 3/2001 | Hur |
| 6,214,023 B1 | 4/2001 | Whipple et al. |
| 6,246,896 B1 | 6/2001 | Dumoulin et al. |
| 6,248,238 B1 | 6/2001 | Burtin et al. |
| 6,325,811 B1 | 12/2001 | Messerly |
| 6,339,368 B1 | 1/2002 | Leith |
| 6,398,755 B1 | 6/2002 | Belef et al. |
| 6,409,742 B1 * | 6/2002 | Fulton, III ............ A61B 19/54 606/116 |
| 6,500,176 B1 | 12/2002 | Truckai et al. |
| 6,500,188 B2 | 12/2002 | Harper et al. |
| 6,514,267 B2 | 2/2003 | Jewett |
| 6,520,185 B1 | 2/2003 | Bommannan et al. |

(56) References Cited

U.S. PATENT DOCUMENTS

| | | | |
|---|---|---|---|
| 6,561,983 B2 | 5/2003 | Cronin et al. | |
| 6,609,414 B2 | 8/2003 | Mayer et al. | |
| 6,623,500 B1 | 9/2003 | Cook et al. | |
| 6,626,901 B1 | 9/2003 | Treat et al. | |
| 6,647,281 B2 | 11/2003 | Morency | |
| 6,650,975 B2 | 11/2003 | Ruffner | |
| 6,656,177 B2 | 12/2003 | Truckai et al. | |
| 6,658,301 B2 | 12/2003 | Loeb et al. | |
| 6,666,875 B1 * | 12/2003 | Sakurai | A61B 17/1628 30/DIG. 1 |
| 6,717,193 B2 | 4/2004 | Olewine et al. | |
| 6,730,042 B2 * | 5/2004 | Fulton | A61B 19/54 600/562 |
| 6,761,698 B2 | 7/2004 | Shibata et al. | |
| 6,783,524 B2 * | 8/2004 | Anderson | A61B 17/320068 606/1 |
| 6,815,206 B2 | 11/2004 | Lin et al. | |
| 6,821,671 B2 | 11/2004 | Hinton et al. | |
| 6,838,862 B2 | 1/2005 | Luu | |
| 6,860,880 B2 | 3/2005 | Treat et al. | |
| 6,869,435 B2 | 3/2005 | Blake | |
| 6,923,807 B2 | 8/2005 | Ryan et al. | |
| 6,945,981 B2 | 9/2005 | Donofrio et al. | |
| 6,982,696 B1 | 1/2006 | Shahoian | |
| 7,031,155 B2 | 4/2006 | Sauciuc et al. | |
| 7,077,853 B2 | 7/2006 | Kramer et al. | |
| 7,083,589 B2 | 8/2006 | Banko et al. | |
| 7,101,371 B2 | 9/2006 | Dycus et al. | |
| 7,112,201 B2 | 9/2006 | Truckai et al. | |
| 7,125,409 B2 | 10/2006 | Truckai et al. | |
| 7,150,712 B2 * | 12/2006 | Buehlmann | A61B 18/148 600/114 |
| 7,169,146 B2 | 1/2007 | Truckai et al. | |
| 7,186,253 B2 | 3/2007 | Truckai et al. | |
| 7,189,233 B2 | 3/2007 | Truckai et al. | |
| 7,220,951 B2 | 5/2007 | Truckai et al. | |
| 7,221,216 B2 | 5/2007 | Nguyen | |
| 7,232,440 B2 | 6/2007 | Dumbauld et al. | |
| 7,244,024 B2 | 7/2007 | Biscardi | |
| 7,292,227 B2 * | 11/2007 | Fukumoto | G01C 21/3664 178/18.04 |
| 7,296,804 B2 | 11/2007 | Lechot et al. | |
| 7,303,556 B2 | 12/2007 | Metzger | |
| 7,309,849 B2 | 12/2007 | Truckai et al. | |
| 7,311,709 B2 | 12/2007 | Truckai et al. | |
| 7,349,741 B2 | 3/2008 | Maltan et al. | |
| 7,354,440 B2 | 4/2008 | Truckai et al. | |
| 7,364,554 B2 | 4/2008 | Bolze et al. | |
| 7,381,209 B2 | 6/2008 | Truckai et al. | |
| 7,416,101 B2 | 8/2008 | Shelton, IV et al. | |
| 7,422,139 B2 | 9/2008 | Shelton, IV et al. | |
| 7,464,846 B2 | 12/2008 | Shelton, IV et al. | |
| 7,473,145 B2 | 1/2009 | Ehr et al. | |
| 7,479,152 B2 * | 1/2009 | Fulton, III | A61B 19/54 606/116 |
| 7,494,492 B2 | 2/2009 | Da Silva et al. | |
| D594,983 S | 6/2009 | Price et al. | |
| 7,563,142 B1 | 7/2009 | Wenger et al. | |
| 7,583,564 B2 | 9/2009 | Ketahara et al. | |
| 7,638,958 B2 | 12/2009 | Philipp et al. | |
| 7,643,378 B2 | 1/2010 | Genosar | |
| 7,717,312 B2 | 5/2010 | Beetel | |
| 7,721,936 B2 | 5/2010 | Shelton, IV et al. | |
| 7,738,971 B2 * | 6/2010 | Swayze | A61B 17/07207 600/1 |
| 7,766,910 B2 * | 8/2010 | Hixson | A61B 18/1445 606/45 |
| 7,766,929 B2 | 8/2010 | Masuda | |
| 7,770,722 B2 | 8/2010 | Donahoe et al. | |
| 7,776,037 B2 | 8/2010 | Odom | |
| 7,780,660 B2 | 8/2010 | Bourne et al. | |
| 7,815,658 B2 | 10/2010 | Murakami | |
| 7,845,537 B2 | 12/2010 | Shelton, IV et al. | |
| 7,846,155 B2 | 12/2010 | Houser et al. | |
| 7,846,159 B2 | 12/2010 | Morrison et al. | |
| 7,889,489 B2 | 2/2011 | Richardson et al. | |
| 7,922,063 B2 | 4/2011 | Zemlok et al. | |
| 7,948,208 B2 | 5/2011 | Partovi et al. | |
| 7,952,322 B2 | 5/2011 | Partovi et al. | |
| 7,952,873 B2 | 5/2011 | Glahn et al. | |
| 7,959,050 B2 * | 6/2011 | Smith | A61B 17/07207 227/175.2 |
| 8,038,025 B2 | 10/2011 | Stark et al. | |
| 8,040,107 B2 | 10/2011 | Ishii | |
| 8,058,771 B2 | 11/2011 | Giordano et al. | |
| 8,075,530 B2 | 12/2011 | Taylor et al. | |
| 8,083,120 B2 | 12/2011 | Shelton et al. | |
| 8,097,011 B2 | 1/2012 | Sanai et al. | |
| 8,142,461 B2 | 3/2012 | Houser et al. | |
| 8,147,488 B2 | 4/2012 | Masuda | |
| 8,177,776 B2 | 5/2012 | Humayun et al. | |
| 8,195,271 B2 | 6/2012 | Rahn | |
| 8,210,411 B2 * | 7/2012 | Yates et al. | 227/175.1 |
| 8,216,212 B2 | 7/2012 | Grant et al. | |
| 8,221,418 B2 | 7/2012 | Prakash et al. | |
| 8,240,498 B2 | 8/2012 | Ramsey et al. | |
| 8,246,642 B2 | 8/2012 | Houser et al. | |
| 8,277,446 B2 | 10/2012 | Heard | |
| 8,292,888 B2 | 10/2012 | Whitman | |
| 8,298,253 B2 | 10/2012 | Charles | |
| 8,301,262 B2 | 10/2012 | Mi et al. | |
| 8,336,725 B2 | 12/2012 | Ramsey et al. | |
| 8,344,690 B2 | 1/2013 | Smith et al. | |
| 8,377,059 B2 | 2/2013 | Deville et al. | |
| 8,400,108 B2 | 3/2013 | Powell et al. | |
| 8,409,222 B2 | 4/2013 | Whitfield et al. | |
| 8,425,545 B2 | 4/2013 | Smith et al. | |
| 8,449,529 B2 | 5/2013 | Bek et al. | |
| 8,487,487 B2 | 7/2013 | Dietz et al. | |
| 8,550,106 B2 | 10/2013 | Hebach et al. | |
| 8,564,242 B2 | 10/2013 | Hansford et al. | |
| 8,641,629 B2 | 2/2014 | Kurokawa | |
| 8,663,112 B2 | 3/2014 | Slayton et al. | |
| 2002/0143359 A1 * | 10/2002 | Fulton, III | A61B 19/54 606/190 |
| 2002/0165577 A1 | 11/2002 | Witt et al. | |
| 2003/0093103 A1 | 5/2003 | Malackowski et al. | |
| 2003/0109802 A1 | 6/2003 | Laeseke et al. | |
| 2003/0114851 A1 | 6/2003 | Truckai et al. | |
| 2004/0097911 A1 | 5/2004 | Murakami et al. | |
| 2004/0116952 A1 | 6/2004 | Sakurai et al. | |
| 2004/0133189 A1 | 7/2004 | Sakurai | |
| 2004/0173487 A1 | 9/2004 | Johnson et al. | |
| 2005/0021065 A1 | 1/2005 | Yamada et al. | |
| 2005/0033195 A1 * | 2/2005 | Fulton | A61B 19/54 600/562 |
| 2005/0256522 A1 | 11/2005 | Francischelli et al. | |
| 2006/0030797 A1 | 2/2006 | Zhou et al. | |
| 2006/0079829 A1 * | 4/2006 | Fulton | A61B 19/54 604/15 |
| 2006/0079874 A1 | 4/2006 | Faller et al. | |
| 2006/0079877 A1 | 4/2006 | Houser et al. | |
| 2006/0079879 A1 | 4/2006 | Faller et al. | |
| 2006/0253176 A1 | 11/2006 | Caruso et al. | |
| 2007/0027447 A1 | 2/2007 | Theroux et al. | |
| 2007/0078484 A1 | 4/2007 | Talarico et al. | |
| 2007/0084742 A1 | 4/2007 | Miller et al. | |
| 2007/0103437 A1 | 5/2007 | Rosenberg | |
| 2007/0191713 A1 | 8/2007 | Eichmann et al. | |
| 2007/0207354 A1 | 9/2007 | Curello et al. | |
| 2007/0261978 A1 | 11/2007 | Sanderson | |
| 2007/0265613 A1 | 11/2007 | Edelstein et al. | |
| 2007/0265620 A1 | 11/2007 | Kraas et al. | |
| 2007/0282333 A1 | 12/2007 | Fortson et al. | |
| 2008/0003491 A1 | 1/2008 | Yahnker et al. | |
| 2008/0004656 A1 | 1/2008 | Livneh | |
| 2008/0057470 A1 | 3/2008 | Levy et al. | |
| 2008/0147058 A1 | 6/2008 | Horrell et al. | |
| 2008/0150754 A1 | 6/2008 | Quendt | |
| 2008/0161783 A1 * | 7/2008 | Cao | A61B 18/22 606/10 |
| 2008/0173651 A1 | 7/2008 | Ping | |
| 2008/0188810 A1 | 8/2008 | Larsen et al. | |

(56) References Cited

U.S. PATENT DOCUMENTS

| | | | |
|---|---|---|---|
| 2008/0200940 A1* | 8/2008 | Eichmann | A61B 17/320068 606/169 |
| 2008/0221491 A1 | 9/2008 | Slayton et al. | |
| 2008/0228104 A1 | 9/2008 | Uber, III et al. | |
| 2008/0255413 A1 | 10/2008 | Zemlok et al. | |
| 2008/0281301 A1 | 11/2008 | Deboer et al. | |
| 2009/0030437 A1 | 1/2009 | Houser et al. | |
| 2009/0043797 A1 | 2/2009 | Dorie et al. | |
| 2009/0076506 A1 | 3/2009 | Baker | |
| 2009/0090763 A1 | 4/2009 | Zemlok et al. | |
| 2009/0105750 A1 | 4/2009 | Price et al. | |
| 2009/0125026 A1 | 5/2009 | Rioux et al. | |
| 2009/0137952 A1* | 5/2009 | Ramamurthy | A61B 5/06 604/95.01 |
| 2009/0138006 A1* | 5/2009 | Bales | A61B 18/1206 606/33 |
| 2009/0143705 A1* | 6/2009 | Danek | A61B 18/08 601/3 |
| 2009/0143797 A1 | 6/2009 | Smith et al. | |
| 2009/0143798 A1 | 6/2009 | Smith et al. | |
| 2009/0143799 A1 | 6/2009 | Smith et al. | |
| 2009/0143800 A1 | 6/2009 | Deville et al. | |
| 2009/0143801 A1 | 6/2009 | Deville et al. | |
| 2009/0143802 A1 | 6/2009 | Deville et al. | |
| 2009/0143803 A1 | 6/2009 | Palmer et al. | |
| 2009/0143804 A1 | 6/2009 | Palmer et al. | |
| 2009/0143805 A1 | 6/2009 | Palmer et al. | |
| 2009/0209979 A1* | 8/2009 | Yates | A61B 17/07207 606/143 |
| 2009/0209990 A1* | 8/2009 | Yates | A61B 17/07207 606/169 |
| 2009/0240246 A1* | 9/2009 | Deville | A61B 18/1445 606/33 |
| 2009/0253030 A1 | 10/2009 | Kooij | |
| 2009/0275940 A1 | 11/2009 | Malackowski et al. | |
| 2009/0281430 A1* | 11/2009 | Wilder | A61B 5/0062 600/463 |
| 2009/0281464 A1 | 11/2009 | Cioanta et al. | |
| 2009/0299195 A1* | 12/2009 | Muller | A61B 5/0062 600/466 |
| 2010/0016855 A1 | 1/2010 | Ramstein et al. | |
| 2010/0021022 A1 | 1/2010 | Pittel et al. | |
| 2010/0030218 A1 | 2/2010 | Prevost | |
| 2010/0069940 A1* | 3/2010 | Miller | A61B 17/320068 606/169 |
| 2010/0069942 A1 | 3/2010 | Shelton | |
| 2010/0076455 A1 | 3/2010 | Birkenbach et al. | |
| 2010/0076474 A1* | 3/2010 | Yates | A61B 17/07207 606/170 |
| 2010/0089970 A1 | 4/2010 | Smith et al. | |
| 2010/0106144 A1 | 4/2010 | Matsumura et al. | |
| 2010/0106146 A1* | 4/2010 | Boitor | A61B 18/22 606/15 |
| 2010/0125172 A1* | 5/2010 | Jayaraj | A61B 1/06 600/249 |
| 2010/0152610 A1 | 6/2010 | Parihar et al. | |
| 2010/0201311 A1 | 8/2010 | Lyell Kirby et al. | |
| 2010/0211053 A1 | 8/2010 | Ross et al. | |
| 2010/0249665 A1 | 9/2010 | Roche | |
| 2010/0268221 A1 | 10/2010 | Beller et al. | |
| 2010/0274160 A1 | 10/2010 | Yachi et al. | |
| 2010/0301095 A1* | 12/2010 | Shelton, IV | A61B 19/026 227/175.4 |
| 2011/0009694 A1 | 1/2011 | Schultz et al. | |
| 2011/0015660 A1 | 1/2011 | Wiener et al. | |
| 2011/0058982 A1 | 3/2011 | Kaneko et al. | |
| 2011/0077514 A1 | 3/2011 | Ulric et al. | |
| 2011/0087212 A1* | 4/2011 | Aldridge | A61B 17/320092 606/34 |
| 2011/0087218 A1 | 4/2011 | Boudreaux et al. | |
| 2011/0152901 A1 | 6/2011 | Woodruff et al. | |
| 2011/0224668 A1 | 9/2011 | Johnson et al. | |
| 2011/0230794 A1* | 9/2011 | van Groningen | A61B 8/546 601/2 |
| 2012/0053585 A1* | 3/2012 | Nycz | A61B 8/0841 606/62 |
| 2012/0071796 A1* | 3/2012 | Smith | A61B 17/320092 601/3 |
| 2012/0116364 A1* | 5/2012 | Houser | A61B 17/00234 606/1 |
| 2012/0179036 A1* | 7/2012 | Patrick | A61M 19/00 600/439 |
| 2012/0265230 A1* | 10/2012 | Yates et al. | 606/170 |
| 2012/0283732 A1* | 11/2012 | Lam | A61B 17/00491 606/49 |
| 2012/0292367 A1 | 11/2012 | Morgan et al. | |
| 2013/0085330 A1* | 4/2013 | Ramamurthy | A61B 5/06 600/117 |
| 2013/0085332 A1* | 4/2013 | Ramamurthy | A61B 5/06 600/117 |
| 2013/0085397 A1* | 4/2013 | Ramamurthy | A61B 5/06 600/476 |
| 2013/0090528 A1* | 4/2013 | Ramamurthy | A61B 5/06 600/117 |
| 2013/0090530 A1* | 4/2013 | Ramamurthy | A61B 5/06 600/182 |
| 2013/0090552 A1* | 4/2013 | Ramamurthy | A61B 5/06 600/424 |
| 2013/0116690 A1* | 5/2013 | Unger | A61B 18/1445 606/46 |
| 2015/0157354 A1* | 6/2015 | Bales, Jr. | A61B 17/320068 606/169 |
| 2015/0305763 A1 | 10/2015 | Houser et al. | |
| 2016/0121143 A1 | 5/2016 | Mumaw et al. | |

FOREIGN PATENT DOCUMENTS

| | | |
|---|---|---|
| DE | 102009013034 | 10/2010 |
| EP | 0897696 A1 | 2/1999 |
| EP | 0947167 A1 | 10/1999 |
| EP | 1330991 A1 | 7/2003 |
| EP | 1525853 A2 | 4/2005 |
| EP | 1535585 A2 | 6/2005 |
| EP | 1684396 A2 | 7/2006 |
| EP | 1721576 A1 | 11/2006 |
| EP | 1743592 A1 | 1/2007 |
| EP | 1818021 A1 | 8/2007 |
| EP | 1839599 | 10/2007 |
| EP | 1868275 A2 | 12/2007 |
| EP | 1886637 A1 | 2/2008 |
| EP | 1943976 A2 | 7/2008 |
| EP | 1970014 | 9/2008 |
| EP | 1997439 A2 | 12/2008 |
| EP | 2027819 A1 | 2/2009 |
| EP | 2090256 A2 | 8/2009 |
| EP | 2105104 A2 | 9/2009 |
| EP | 2165660 A2 | 3/2010 |
| EP | 2218409 A1 | 8/2010 |
| EP | 2243439 A1 | 10/2010 |
| EP | 2345454 A1 | 7/2011 |
| GB | 2425874 | 11/2006 |
| GB | 2440566 A | 2/2008 |
| JP | 3744974 B | 2/1997 |
| WO | WO 97/24072 | 7/1997 |
| WO | WO 00/65682 | 2/2000 |
| WO | WO 03/013374 | 2/2003 |
| WO | WO 03/020139 | 3/2003 |
| WO | WO 2004/113991 | 12/2004 |
| WO | WO 2005/079915 | 9/2005 |
| WO | WO 2006/023266 | 3/2006 |
| WO | WO 2007/004515 | 1/2007 |
| WO | WO 2007/024983 | 3/2007 |
| WO | WO 2007/090025 | 8/2007 |
| WO | WO 2007/137115 | 11/2007 |
| WO | WO 2007/137304 | 11/2007 |
| WO | WO 2008/071898 | 6/2008 |
| WO | WO 2008/102154 | 8/2008 |
| WO | WO 2008/107902 | 9/2008 |
| WO | WO 2008/131357 | 10/2008 |
| WO | WO 2009/018409 | 2/2009 |

(56) References Cited

FOREIGN PATENT DOCUMENTS

| WO | WO 2009/046394 | 4/2009 |
|----|----------------|--------|
| WO | WO 2009/070780 | 6/2009 |
| WO | WO 2009/073608 | 6/2009 |
| WO | WO 2010/030850 | 3/2010 |
| WO | WO 2010/096174 | 8/2010 |
| WO | WO 2011/059785 | 5/2011 |
| WO | WO 2011/089270 | 7/2011 |

OTHER PUBLICATIONS

International Search Report and Written Opinion dated Feb. 2, 2012 for Application No. PCT/US2011/059378.
International Search Report dated Feb. 2, 2012 for Application No. PCT/US2011/059354.
International Search Report dated Feb. 7, 2012 for Application No. PCT/US2011/059351.
International Search Report dated Feb. 13, 2012 for Application No. PCT/US2011/059217.
International Search Report dated Feb. 23, 2012 for Application No. PCT/US2011/059371.
International Search Report dated Mar. 15, 2012 for Application No. PCT/US2011/059338.
International Search Report dated Mar. 22, 2012 for Application No. PCT/US2011/059362.
International Search Report dated Apr. 4, 2012 for Application No. PCT/US2011/059215.
International Search Report dated Apr. 11, 2012 for Application No. PCT/US2011/059381.
International Search Report dated Apr. 18, 2012 for Application No. PCT/US2011/059222.
International Search Report dated May 24, 2012 for Application No. PCT/US2011/059378.
International Search Report dated Jun. 4, 2012 for Application No. PCT/US2011/059365.
International Search Report dated Jun. 12, 2012 for Application No. PCT/US2011/059218.
Communication from International Searching Authority dated Feb. 6, 2012 for Application No. PCT/US2011/059362.
Communication from International Searching Authority dated Feb. 2, 2012 for Application No. PCT/US2011/059222.
Communication from International Searching Authority dated Jan. 24, 2012 for Application No. PCT/US2011/059215.
Communication from International Searching Authority dated Feb. 2, 2012 for Application No. PCT/US2011/059378.
Machine Translation of the Abstract of German Application No. DE 102009013034.
Machine Translation of German Application No. DE 102008051866.
U.S. Appl. No. 13/151,471, filed Jun. 2, 2011, Stulen.
U.S. Appl. No. 13/151,481, filed Jun. 2, 2011, Yates et al.
U.S. Appl. No. 13/151,488, filed Jun. 2, 2011, Shelton IV et al.
U.S. Appl. No. 13/151,498, filed Jun. 2, 2011, Felder et al.
U.S. Appl. No. 13/151,503, filed Jun. 2, 2011, Madan et al.
U.S. Appl. No. 13/151,509, filed Jun. 2, 2011, Smith et al.
U.S. Appl. No. 13/151,512, filed Jun. 2, 2011, Houser et al.
U.S. Appl. No. 13/151,515, filed Jun. 2, 2011, Felder et al.
U.S. Appl. No. 13/176,875, filed Jul. 6, 2011, Smith et al.
U.S. Appl. No. 13/269,870, filed Oct. 10, 2011, Houser et al.
U.S. Appl. No. 13/269,883, filed Oct. 10, 2011, Mumaw et al.
U.S. Appl. No. 13/269,899, filed Oct. 10, 2011, Boudreaux et al.
U.S. Appl. No. 13/270,667, filed Oct. 11, 2011, Timm et al.
U.S. Appl. No. 13/270,684, filed Oct. 11, 2011, Madan et al.
U.S. Appl. No. 13/270,701, filed Oct. 11, 2011, Johnson et al.
U.S. Appl. No. 13/271,352, filed Oct. 12, 2011, Houser et al.
U.S. Appl. No. 13/271,364, filed Oct. 12, 2011, Houser et al.
U.S. Appl. No. 13/274,480, filed Oct. 17, 2011, Mumaw et al.
U.S. Appl. No. 13/274,496, filed Oct. 17, 2011, Houser et al.
U.S. Appl. No. 13/274,507, filed Oct. 17, 2011, Houser et al.
U.S. Appl. No. 13/274,516, filed Oct. 17, 2011, Haberstich et al.
U.S. Appl. No. 13/274,540, filed Oct. 17, 2011, Madan.
U.S. Appl. No. 13/274,805, filed Oct. 17, 2011, Price et al.
U.S. Appl. No. 13/274,830, filed Oct. 17, 2011, Houser et al.
U.S. Appl. No. 13/275,495, filed Oct. 18, 2011, Houser et al.
U.S. Appl. No. 13/275,514, filed Oct. 18, 2011, Houser et al.
U.S. Appl. No. 13/275,547, filed Oct. 18, 2011, Houser et al.
U.S. Appl. No. 13/275,563, filed Oct. 18, 2011, Houser et al.
U.S. Appl. No. 13/276,660, filed Oct. 19, 2011, Houser et al.
U.S. Appl. No. 13/276,673, filed Oct. 19, 2011, Kimball et al.
U.S. Appl. No. 13/276,687, filed Oct. 19, 2011, Price et al.
U.S. Appl. No. 13/276,707, filed Oct. 19, 2011, Houser et al.
U.S. Appl. No. 13/276,725, filed Oct. 19, 2011, Houser et al.
U.S. Appl. No. 13/276,745, filed Oct. 19, 2011, Stulen et al.
U.S. Appl. No. 13/277,328, filed Oct. 20, 2011, Houser et al.
Dietz, T. et al., Partially Implantable Vibrating Ossicular Prosthesis, Transducers'97, vol. 1, International Conference on Solid State Sensors and Actuators, (Jun. 16-19, 1997) pp. 433-436 (Abstract).
"System 6 Aseptic Battery System," Stryker (2006) pp. 1-2.
International Search Report dated Jan. 12, 2012 for Application No. PCT/US2011/059226.
International Search Report dated Jan. 26, 2012 for Application No. PCT/US2011/059220.
International Search Report dated Feb. 1, 2012 for Application No. PCT/US2011/059223.
International Search Report dated May 29, 2012 for Application No. PCT/US2011/059358.
International Search Report and Written Opinion dated Jul. 6, 2012 for Application No. PCT/US2011/059381.
Office Action Non-Final dated Aug. 6, 2013 for U.S. Appl. No. 13/151,471.
Restriction Requirement dated Dec. 11, 2012 for U.S. Appl. No. 13/151,481.
Office Action Non-Final dated Feb. 15, 2013 for U.S. Appl. No. 13/151,481.
Office Action Final dated Jun. 7, 2013 for U.S. Appl. No. 13/151,481.
Restriction Requirement dated Jul. 5, 2013 for U.S. Appl. No. 13/151,488.
Office Action Non-Final dated Jun. 14, 2013 for U.S. Appl. No. 13/151,498.
Restriction Requirement dated Mar. 13, 2013 for U.S. Appl. No. 13/151,509.
Restriction Requirement dated Jun. 24, 2013 for U.S. Appl. No. 13/151,509.
Restriction Requirement dated Feb. 28, 2013 for U.S. Appl. No. 13/270,667.
Office Action Non-Final dated Apr. 26, 2013 for U.S. Appl. No. 13/270,667.
Office Action Non-Final dated Dec. 21, 2012 for U.S. Appl. No. 13/274,516.
Office Action Final dated Aug. 16, 2013 for U.S. Appl. No. 13/274,516.
Restriction Requirement dated Feb. 25, 2013 for U.S. Appl. No. 13/274,540.
Office Action Non-Final dated Apr. 30, 2013 for U.S. Appl. No. 13/274,540.
Office Action Non-Final dated Apr. 1, 2013 for U.S. Appl. No. 13/274,805.
Office Action Final dated Sep. 12, 2013 for U.S. Appl. No. 13/274,805.
Restriction Requirement dated Apr. 29, 2013 for U.S. Appl. No. 13/274,830.
Office Action Non-Final dated Jun. 14, 2013 for U.S. Appl. No. 13/274,830.
Restriction Requirement dated Apr. 4, 2013 for U.S. Appl. No. 13/275,495.
Office Action Non-Final dated May 31, 2013 for U.S. Appl. No. 13/275,495.
Office Action Non-Final dated May 17, 2013 for U.S. Appl. No. 13/275,547.
Office Action Non-Final dated Feb. 1, 2013 for U.S. Appl. No. 13/275,563.

(56) References Cited

OTHER PUBLICATIONS

Office Action Final dated Aug. 29, 2013 for U.S. Appl. No. 13/275,563.
Restriction Requirement dated Feb. 6, 2013 for U.S. Appl. No. 13/276,660.
Office Action Non-Final dated Jun. 3, 2013 for U.S. Appl. No. 13/276,660.
Restriction Requirement dated Feb. 6, 2013 for U.S. Appl. No. 13/276,687.
Office Action Non-Final dated Jun. 12, 2013 for U.S. Appl. No. 13/276,687.
Restriction Requirement dated Feb. 21, 2013 for U.S. Appl. No. 13/276,707.
Office Action Non-Final dated May 6, 2013 for U.S. Appl. No. 13/276,707.
Restriction Requirement dated Feb. 6, 2013 for U.S. Appl. No. 13/276,725.
Restriction Requirement dated Dec. 21, 2012 for U.S. Appl. No. 13/276,745.
Office Action Non-Final dated Apr. 30, 2013 for U.S. Appl. No. 13/276,745.
U.S. Appl. No. 13/151,471.
U.S. Appl. No. 13/151,481.
U.S. Appl. No. 13/151,488.
U.S. Appl. No. 13/151,498.
U.S. Appl. No. 13/151,503.
U.S. Appl. No. 13/151,509.
U.S. Appl. No. 13/151,512.
U.S. Appl. No. 13/269,870.
U.S. Appl. No. 13/270,667.
U.S. Appl. No. 13/270,684.
U.S. Appl. No. 13/270,701.
U.S. Appl. No. 13/271,352.
U.S. Appl. No. 13/271,364.
U.S. Appl. No. 13/274,480.
U.S. Appl. No. 13/274,496.
U.S. Appl. No. 13/274,507.
U.S. Appl. No. 13/274,516.
U.S. Appl. No. 13/274,540.
U.S. Appl. No. 13/274,805.
U.S. Appl. No. 13/274,830.
U.S. Appl. No. 13/275,495.
U.S. Appl. No. 13/275,514.
U.S. Appl. No. 13/275,547.
U.S. Appl. No. 13/275,563.
U.S. Appl. No. 13/276,660.
U.S. Appl. No. 13/276,687.
U.S. Appl. No. 13/276,707.
U.S. Appl. No. 13/276,725.
U.S. Appl. No. 13/276,745; and.
U.S. Appl. No. 13/277,328.
European Communication dated Feb. 19, 2014 for Application No. EP 11781972.2.
International Preliminary Report on Patentability for Application No. PCT/US2011/059212 dated May 7, 2013.
International Preliminary Report on Patentability for Application No. PCT/US2011/059215 dated May 8, 2013.
International Preliminary Report on Patentability for Application No. PCT/US2011/059217 dated May 7, 2013.
International Preliminary Report on Patentability for Application No. PCT/US2011/059218 dated May 7, 2013.
International Preliminary Report on Patentability for Application No. PCT/US2011/059220 dated May 7, 2013.
International Preliminary Report on Patentability for Application No. PCT/US2011/059222 dated May 7, 2013.
International Preliminary Report on Patentability for Application No. PCT/US2011/059223 dated May 7, 2013.
International Preliminary Report on Patentability for Application No. PCT/US2011/059226 dated May 7, 2013.
International Preliminary Report on Patentability for Application No. PCT/US2011/059338 dated May 7, 2013.
International Preliminary Report on Patentability for Application No. PCT/US2011/059351 dated May 7, 2013.
International Preliminary Report on Patentability for Application No. PCT/US2011/059354 dated May 7, 2013.
International Preliminary Report on Patentability for Application No. PCT/US2011/059358 dated May 7, 2013.
International Preliminary Report on Patentability for Application No. PCT/US2011/059362 dated May 7, 2013.
International Preliminary Report on Patentability for Application No. PCT/US2011/059365 dated May 8, 2013.
International Preliminary Report on Patentability for Application No. PCT/US2011/059371 dated May 7, 2013.
International Preliminary Report on Patentability for Application No. PCT/US2011/059378 dated May 7, 2013.
International Preliminary Report on Patentability for Application No. PCT/US2011/059381 dated May 8, 2013.
Notice of Allowance dated Dec. 6, 2013 for U.S. Appl. No. 13/151,471.
Office Action Non-Final dated Mar. 28, 2014 for U.S. Appl. No. 13/151,471.
Office Action Final dated Nov. 21, 2013 for U.S. Appl. No. 13/151,498.
Office Action Non Final dated Mar. 18, 2014 for U.S. Appl. No. 13/151,498.
Office Action Non Final dated Jun. 18, 2014 for U.S. Appl. No. 13/151,503.
Office Action Non Final dated Sep. 26, 2013 for U.S. Appl. No. 13/151,509.
Office Action Final dated Jan. 29, 2014 for U.S. Appl. No. 13/151,509.
Restriction Requirement dated Jun. 11, 2014 for U.S. Appl. No. 13/151,512.
Office Action Non Final dated Oct. 25, 2013 for U.S. Appl. No. 13/270,667.
Office Action Non Final dated Nov. 21, 2013 for U.S. Appl. No. 13/271,352.
Office Action Non-Final dated Feb. 14, 2014 for U.S. Appl. No. 13/274,480.
Restriction Requirement dated Dec. 9, 2013 for U.S. Appl. No. 13/274,496.
Office Action Non-Final dated Feb. 6, 2014 for U.S. Appl. No. 13/274,496.
Office Action Final dated May 15, 2014 for U.S. Appl. No. 13/274,496.
Restriction Requirement dated Mar. 28, 2014 for U.S. Appl. No. 13/274,507.
Office Action Non-Final dated Jun. 19, 2014 for U.S. Appl. No. 13/274,507.
Office Action Non Final dated Dec. 6, 2013 for U.S. Appl. No. 13/274,516.
Office Action Final dated Jun. 12, 2014 for U.S. Appl. No. 13/274,516.
Office Action Final dated Oct. 25, 2013 for U.S. Appl. No. 13/274,540.
Office Action Final dated Nov. 26, 2013 for U.S. Appl. No. 13/274,830.
Office Action Final dated Dec. 5, 2013 for U.S. Appl. No. 13/275,495.
Office Action Non-Final dated Jan. 6, 2014 for U.S. Appl. No. 13/275,514.
Office Action Final dated Feb. 28, 2014 for U.S. Appl. No. 13/275,547.
Notice of Allowance dated Nov. 12, 2013 for U.S. Appl. No. 13/276,687.
Notice of Allowance dated Jun. 2, 2014 for U.S. Appl. No. 13/276,687.
Office Action Final dated Sep. 27, 2013 for U.S. Appl. No. 13/276,707.
Office Action Final dated 1108/2013 for U.S. Appl. No. 13/274,745.
Office Action Non-Final dated Feb. 28, 2014 for U.S. Appl. No. 13/276,745.

(56) References Cited

OTHER PUBLICATIONS

US Office Action, Notice of Allowance, dated Aug. 19, 2014 for U.S. Appl. No. 13/151,471.
US Office Action, Notice of Allowance, dated Nov. 21, 2014 for U.S. Appl. No. 13/151,471.
US Office Action, Non-Final, dated Aug. 14, 2014 for U.S. Appl. No. 13/151,481.
US Office Action, Non-Final, dated Nov. 7, 2014 for U.S. Appl. No. 13/151,488.
US Office Action, Notice of Allowance, dated Aug. 6, 2014 for U.S. Appl. No. 13/151,498.
US Office Action, Notice of Allowance, dated Nov. 21, 2014 for U.S. Appl. No. 13/151,498.
US Office Action, Non-Final, dated Nov. 6, 2014 for U.S. Appl. No. 13/151,503.
US Office Action, Non-Final, dated Jul. 9, 2014 for U.S. Appl. No. 13/151,509.
US Office Action, Notice of Allowance, dated Oct. 28, 2014 for U.S. Appl. No. 13/151,509.
US Office Action, Notice of Allowance, dated Oct. 29, 2014 for U.S. Appl. No. 13/151,512.
US Office Action, Restriction Requirement, dated Jul. 11, 2014 for U.S. Appl. No. 13/269,870.
US Office Action, Non-Final, dated Jul. 29, 2014 for U.S. Appl. No. 13/270,667.
US Office Action, Restriction Requirement, dated Jul. 9, 2014 for U.S. Appl. No. 13/270,684.
US Office Action, Non-Final, dated Oct. 9, 2014 for U.S. Appl. No. 13/270,684.
US Office Action, Restriction Requirement, dated Sep. 11, 2014 for U.S. Appl. No. 13/270,701.
US Office Action, Restriction Requirement, dated Sep. 25, 2014 for U.S. Appl. No. 13/271,352.
US Office Action, Restriction Requirement, dated Oct. 2, 2013 for U.S. Appl. No. 13/274,480.
US Office Action, Final, dated Jul. 17, 2014 for U.S. Appl. No. 13/274,480.
US Office Action, Final, dated Aug. 22, 2014 for U.S. Appl. No. 13/274,496.
US Office Action, Non-Final, dated Oct. 8, 2014 for U.S. Appl. No. 13/274,516.
US Office Action, Non-Final, dated Aug. 26, 2014 for U.S. Appl. No. 13/274,540.
US Office Action, Non-Final, dated Aug. 14, 2014 for U.S. Appl. No. 13/274,805.
US Office Action, Non-Final, dated Oct. 22, 2014 for U.S. Appl. No. 13/274,830.
US Office Action, Non-Final, dated Sep. 9, 2014 for U.S. Appl. No. 13/275,514.
US Office Action, Non-Final, dated Aug. 20, 2014 for U.S. Appl. No. 13/275,547.
US Office Action, Non-Final, dated Oct. 23, 2014 for U.S. Appl. No. 13/275,563.
US Office Action, Restriction Requirement, dated Jul. 9, 2014 for U.S. Appl. No. 13/276,660.
US Office Action, Notice of Allowance, dated Sep. 12, 2014 for U.S. Appl. No. 13/276,687.
US Office Action, Non-Final, dated Aug. 20, 2014 for U.S. Appl. No. 13/276,725.
US Office Action, Notice of Allowance, dated Oct. 7, 2014 for U.S. Appl. No. 13/276,745.
US Office Action, Restriction Requirement, dated Sep. 24, 2014 for U.S. Appl. No. 13/277,328.
U.S. Non-Provisional Pat. Appl. No. 13/151,488.
U.S. Non-Provisional Pat. Appl. No. 13/151,503.
U.S. Non-Provisional Pat. Appl. No. 13/269,870.
U.S. Non-Provisional Pat. Appl. No. 13/270,701.
U.S. Non-Provisional Pat. Appl. No. 13/271,364.
U.S. Non-Provisional Pat. Appl. No. 13/274,480.
U.S. Non-Provisional Pat. Appl. No. 13/274,496.
U.S. Non-Provisional Pat. Appl. No. 13/274,507.
U.S. Non-Provisional Pat. Appl. No. 13/275,495.
U.S. Non-Provisional Pat. Appl. No. 13/275,514.
U.S. Non-Provisional Pat. Appl. No. 13/275,547.
U.S. Non-Provisional Pat. Appl. No. 13/275,563.
U.S. Non-Provisional Pat. Appl. No. 13/276,707.
U.S. Non-Provisional Pat. Appl. No. 13/277,328.
U.S. Non-Provisional Pat. Appl. No. 14/788,915.
U.S. Non-Provisional Pat. Appl. No. 14/992,104.
U.S. Non-Provisional Pat. Appl. No. 15/008,530.
U.S. Appl. No. 8,998,939.
U.S. Appl. No. 9,000,720.
U.S. Appl. No. 9,011,427.
U.S. Appl. No. 9,011,471.
U.S. Appl. No. 9,017,849.
U.S. Appl. No. 9,017,851.
U.S. Appl. No. 9,039,720.
U.S. Appl. No. 9,072,523.
U.S. Appl. No. 9,089,338.
U.S. Appl. No. 9,095,346.
U.S. Appl. No. 9,161,803.
U.S. Appl. No. 9,192,428.
U.S. Appl. No. 9,247,986.
U.S. Appl. No. 9,308,009.
U.S. Appl. No. 9,346,279.
U.S. Appl. No. 9,375,255.
Chinese First Office Action dated Mar. 27, 2015 for Application No. CN2011800638214.
Chinese First Office Action dated Mar. 4, 2015 for Application No. CN201180063595.X.
Chinese First Office Action dated Jan. 29, 2015 for Application No. CN2011800638159.
Japanese Office Action, Notification of Reasons for Refusal, dated Sep. 29, 2015 for Application No. 2013-537871.
Japanese Office Action, Notification of Reasons for Refusal, dated Sep. 29, 2015 for Application No. 2013-537872.
Japanese Office Action, Notification of Reasons for Refusal, dated Oct. 27, 2015 for Application No. 2013-537873.
US Office Action, Notice of Allowance, dated Feb. 8, 2016 for U.S. Appl. No. 13/276,660.
US Office Action, Notice of Allowance, dated Dec. 23, 2014 for U.S. Appl. No. 13/276,687.

\* cited by examiner

USER FEEDBACK THROUGH END EFFECTOR OF SURGICAL INSTRUMENT

PRIORITY

This application claims priority to U.S. Provisional Application Ser. No. 61/410,603, filed Nov. 5, 2010, entitled "Energy-Based Surgical Instruments," the disclosure of which is incorporated by reference herein.

This application also claims priority to U.S. Provisional Application Ser. No. 61/487,846, filed May 19, 2011, entitled "Energy-Based Surgical Instruments," the disclosure of which is incorporated by reference herein.

BACKGROUND

In some settings, endoscopic surgical instruments may be preferred over traditional open surgical devices since a smaller incision may reduce the post-operative recovery time and complications. Consequently, some endoscopic surgical instruments may be suitable for placement of a distal end effector at a desired surgical site through a cannula of a trocar. These distal end effectors may engage tissue in a number of ways to achieve a diagnostic or therapeutic effect (e.g., endocutter, grasper, cutter, stapler, clip applier, access device, drug/gene therapy delivery device, and energy delivery device using ultrasound, RF, laser, etc.). Endoscopic surgical instruments may include a shaft between the end effector and a handle portion, which is manipulated by the clinician. Such a shaft may enable insertion to a desired depth and rotation about the longitudinal axis of the shaft, thereby facilitating positioning of the end effector within the patient.

Examples of endoscopic surgical instruments include those disclosed in U.S. Pat. Pub. No. 2006/0079874, entitled "Tissue Pad Use with an Ultrasonic Surgical Instrument," published Apr. 13, 2006, the disclosure of which is incorporated by reference herein; U.S. Pat. Pub. No. 2007/0191713, entitled "Ultrasonic Device for Cutting and Coagulating," published Aug. 16, 2007, the disclosure of which is incorporated by reference herein; U.S. Pat. Pub. No. 2007/0282333, entitled "Ultrasonic Waveguide and Blade," published Dec. 6, 2007, the disclosure of which is incorporated by reference herein; U.S. Pat. Pub. No. 2008/0200940, entitled "Ultrasonic Device for Cutting and Coagulating," published Aug. 21, 2008, the disclosure of which is incorporated by reference herein; U.S. Pub. No. 2009/0209990 entitled "Motorized Surgical Cutting and Fastening Instrument Having Handle Based Power Source," published Aug. 20, 2009, now U.S. Pat. No. 8,657,174, issued Feb. 25, 2014, the disclosure of which is incorporated by reference herein; and U.S. Pub. No. 2010/0069940 entitled "Ultrasonic Device for Fingertip Control," published Mar. 18, 2010, now U.S. Pat. No. 9,023,071, issued May 5, 2015, the disclosure of which is incorporated by reference herein; U.S. Pat. Pub. No. 2011/0015660, entitled "Rotating Transducer Mount for Ultrasonic Surgical Instruments," published Jan. 20, 2011, now U.S. Pat. No. 8,461,744, issued June 11, 2013, the disclosure of which is incorporated by reference herein; U.S. Pat. No. 6,500,176, entitled "Electrosurgical Systems and Techniques for Sealing Tissue," issued Dec. 31, 2002, the disclosure of which is incorporated by reference herein; U.S. Pat. No. 7,416,101 entitled "Motor-Driven Surgical Cutting and Fastening Instrument with Loading Force Feedback," issued Aug. 26, 2008, the disclosure of which is incorporated by reference herein; U.S. Pat. No. 7,738,971 entitled "Post-Sterilization Programming of Surgical Instruments," issued Jun. 15, 2010, the disclosure of which is incorporated by reference herein; and U.S. Pat. Pub. No. 2011/0087218, entitled "Surgical Instrument Comprising First and Second Drive Systems Actuatable by a Common Trigger Mechanism," published Apr. 14, 2011, now U.S. Pat. No. 8,939,974, issued Jan. 27, 2015, the disclosure of which is incorporated by reference herein. Additionally, such surgical tools may include a cordless transducer such as that disclosed in U.S. Pat. Pub. No. 2009/0143797, entitled "Cordless Hand-held Ultrasonic Cautery Cutting Device," published Jun. 4, 2009, now U.S. Pat. No. 8,419,757, issued Apr. 16, 2013, the disclosure of which is incorporated by reference herein. In addition, the surgical instruments may be used, or adapted for use, in robotic-assisted surgery settings such as that disclosed in U.S. Pat. No. 6,783,524, entitled "Robotic Surgical Tool with Ultrasound Cauterizing and Cutting Instrument," issued Aug. 31, 2004.

While several systems and methods have been made and used for surgical instruments, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

Figure 1:
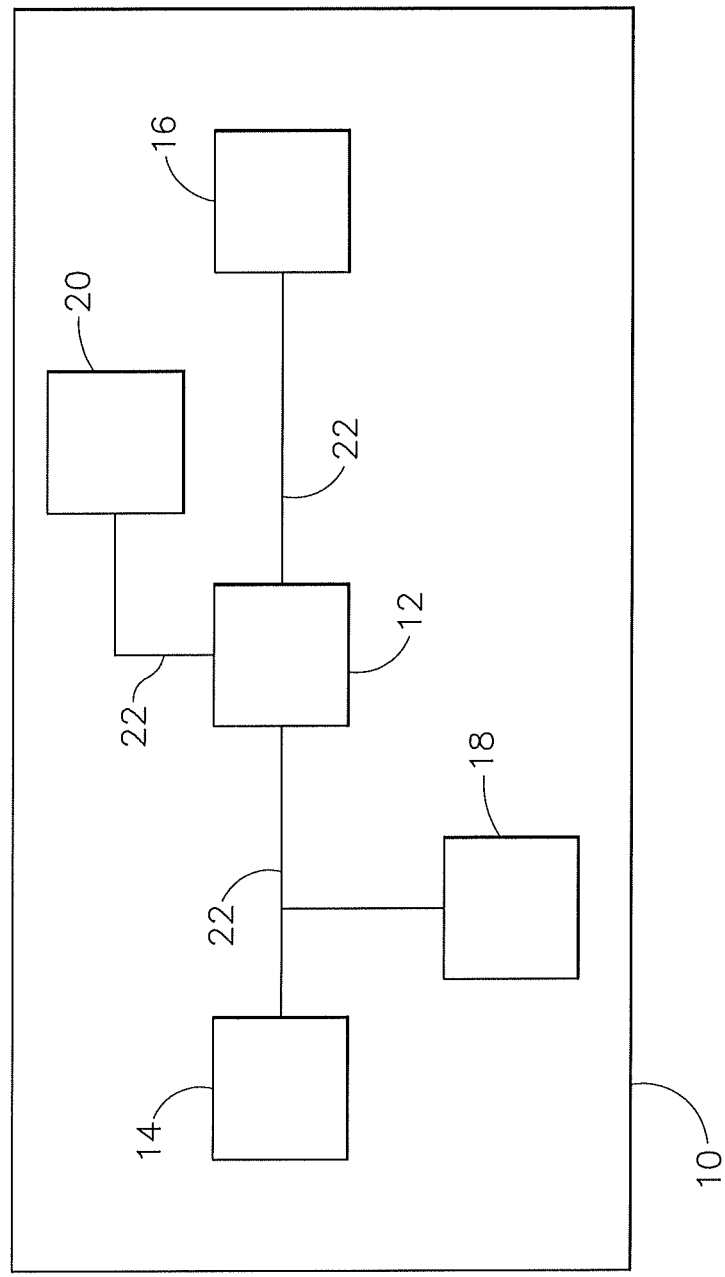
FIG. 1 depicts a schematic view of an exemplary medical device having an internal power source.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

I. Exemplary Medical Device Overview

FIG. 1 shows components of an exemplary medical device (10) in diagrammatic block form. As shown, medical device (10) comprises a control module (12), a power source (14), and an end effector (16). Merely exemplary power sources (14) may include NiMH batteries, Li-ion batteries (e.g., prismatic cell type lithium ion batteries, etc.), Ni-Cad batteries, or any other type of power source as may be apparent to one of ordinary skill in the art in light of the teachings herein. Control module (12) may comprise a microprocessor, an application specific integrated circuit (ASIC), memory, a printed circuit board (PCB), a storage device (such as a solid state drive or hard disk), firmware, software, or any other suitable control module components as will be apparent to one of ordinary skill in the art in light of the teachings herein. Control module (12) and power source (14) are coupled by an electrical connection (22), such as a cable and/or traces in a circuit board, etc., to transfer power from power source (14) to control module (12). Alternatively, power source (14) may be selectively coupled to control module (12). This allows power source (14) to be detached and removed from medical device (10), which may further allow power source (14) to be readily recharged or reclaimed for resterilization and reuse, such as in accordance with the various teachings herein. In addition or in the alternative, control module (12) may be removed for servicing, testing, replacement, or any other purpose as will be apparent to one of ordinary skill in the art in view of the teachings herein.

End effector (16) is coupled to control module (12) by another electrical connection (22). End effector (16) is configured to perform a desired function of medical device (10). By way of example only, such function may include cauterizing tissue, ablating tissue, severing tissue, ultrasonically vibrating, stapling tissue, or any other desired task for medical device (10). End effector (16) may thus include an active feature such as an ultrasonic blade, a pair of clamping jaws, a sharp knife, a staple driving assembly, a monopolar RF electrode, a pair of bipolar RF electrodes, a thermal heating element, and/or various other components. End effector (16) may also be removable from medical device (10) for servicing, testing, replacement, or any other purpose as will be apparent to one of ordinary skill in the art in view of the teachings herein. In some versions, end effector (16) is modular such that medical device (10) may be used with different kinds of end effectors (e.g., as taught in U.S. Provisional Application Ser. No. 61/410,603, etc.). Various other configurations of end effector (16) may be provided for a variety of different functions depending upon the purpose of medical device (10) as will be apparent to those of ordinary skill in the art in view of the teachings herein. Similarly, other types of components of a medical device (10) that may receive power from power source (14) will be apparent to those of ordinary skill in the art in view of the teachings herein.

Medical device (10) of the present example includes a trigger (18) and a sensor (20), though it should be understood that such components are merely optional. Trigger (18) is coupled to control module (12) and power source (14) by electrical connection (22). Trigger (18) may be configured to selectively provide power from power source (14) to end effector (16) (and/or to some other component of medical device (10)) to activate medical device (10) when performing a procedure. Sensor (20) is also coupled to control module (12) by an electrical connection (22) and may be configured to provide a variety of information to control module (12) during a procedure. By way of example only, such configurations may include sensing a temperature at end effector (16) or determining the oscillation rate of end effector (16). Data from sensor (20) may be processed by control module (12) to effect the delivery of power to end effector (16) (e.g., in a feedback loop, etc.). Various other configurations of sensor (20) may be provided depending upon the purpose of medical device (10) as will be apparent to those of ordinary skill in the art in view of the teachings herein. Of course, as with other components described herein, medical device (10) may have more than one sensor (20), or sensor (20) may simply be omitted if desired.

Figure 2:
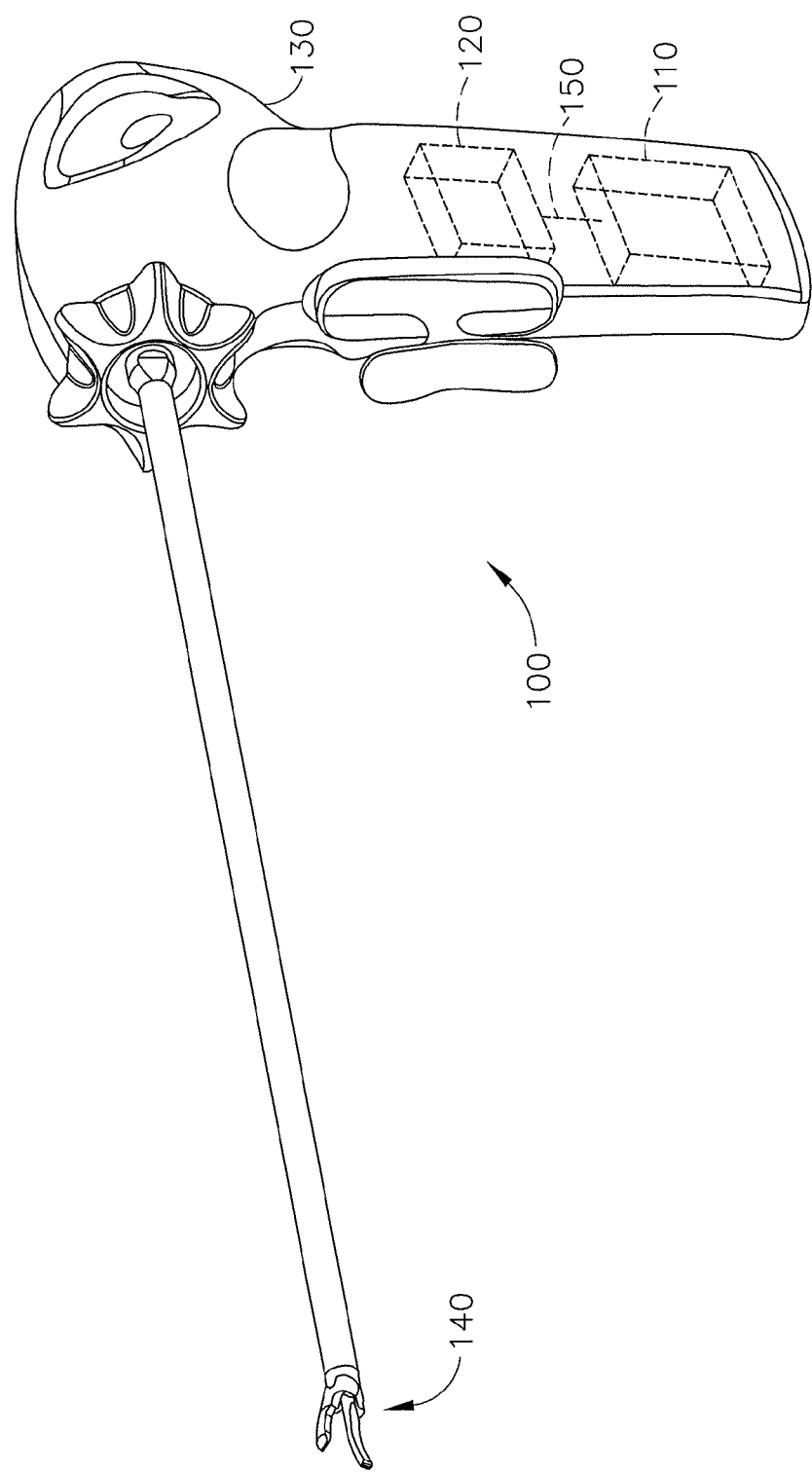
FIG. 2 depicts a perspective view of an exemplary medical device having an internal power source.

FIG. 2 depicts a merely exemplary form that medical device (10) may take. In particular, FIG. 2 shows a medical device (100) comprising a power source (110), a control module (120), a housing (130), end effector (140), and an electrical connection (150). In the present example, power source (110) is located internally within housing (130) of medical device (100). Alternatively, power source (110) may only partially extend into housing (130) and may be selectively attachable to a portion of housing (130). In yet a further exemplary configuration, a portion of housing (130) may extend into power source (110) and power source (110) may be selectively attachable to the portion of housing (130). Power source (110) may also be configured to detach from medical device (100) and decouple from control module (120) or electrical connection (150). As a result, power source (110) may be completely separated from medical device (100) in some versions. By way of example only, power source (110) may be constructed in accordance with the teachings of U.S. Pub. No. 2011/0087212, entitled "Surgical Generator for Ultrasonic and Electrosurgical Devices," published Apr. 14, 2011, now U.S. Pat. No. 8,986,302, issued Mar. 24, 2015, the disclosure of which is incorporated by reference herein. In some versions, power source (110) may be removed to be recharged or reclaimed for resterilization and reuse, such as in accordance with various teachings herein. After recharging, or after an initial charge, power source (110) may be inserted or reinserted into medical device (100) and secured to housing (130) or internally within housing (130). Of course, medical device (100) may also allow power source (110) to be charged and/or recharged while power source (110) is still in or otherwise coupled relative to housing (130).

It should also be understood that control module (120) may be removed for servicing, testing, replacement, or any other purpose as will be apparent to one of ordinary skill in the art in view of the teachings herein. Further, end effector (140) may also be removable from medical device (100) for servicing, testing, replacement, or any other purpose as will be apparent to one of ordinary skill in the art in view of the teachings herein.

While certain configurations of an exemplary medical device (100) have been described, various other ways in which medical device (100) may be configured will be apparent to those of ordinary skill in the art in view of the teachings herein. By way of example only, medical devices (10, 100) and/or any other medical device referred to herein may be constructed in accordance with at least some of the teachings of U.S. Pat. No. 5,322,055 entitled "Clamp Coagulator/Cutting System for Ultrasonic Surgical Instruments," issued Jun. 21, 1994, the disclosure of which is incorporated by reference herein; U.S. Pat. No. 5,873,873 entitled "Ultrasonic Clamp Coagulator Apparatus Having Improved Clamp Mechanism," issued Feb. 23, 1999, the disclosure of which is incorporated by reference herein; U.S. Pat. No. 5,980,510, entitled "Ultrasonic Clamp Coagulator Apparatus Having Improved Clamp Arm Pivot Mount," filed Oct. 10, 1997, the disclosure of which is incorporated by reference herein; U.S. Pat. No. 6,325,811 entitled "Blades with Functional Balance Asymmetries for use with Ultrasonic Surgical Instruments," issued Dec. 4, 2001, the disclosure of which is incorporated by reference herein; U.S. Pub. No. 2006/0079874 entitled "Tissue Pad for Use with an Ultrasonic Surgical Instrument," published Apr. 13, 2006, the disclosure of which is incorporated by reference herein; U.S. Pub. No. 2007/0191713 entitled "Ultrasonic Device for Cutting and Coagulating," published Aug. 16, 2007, the disclosure of which is incorporated by reference herein; U.S. Pub. No. 2007/0282333 entitled "Ultrasonic Waveguide and Blade," published Dec. 6, 2007, the disclosure of which is incorporated by reference herein; U.S. Pub. No. 2008/0200940 entitled "Ultrasonic Device for Cutting and Coagulating," published Aug. 21, 2008, the disclosure of which is incorporated by reference herein; U.S. Pub. No. 2009/0143797, entitled "Cordless Hand-held Ultrasonic Cautery Cutting Device," published Jun. 4, 2009, now U.S. Pat. No. 8,419,757, issued Apr. 16, 2013, the disclosure of which is incorporated by reference herein; U.S. Pub. No. 2010/0069940 entitled "Ultrasonic Device for Fingertip Control," published Mar. 18, 2010, now U.S. Pat. No. 9,023,071, issued May 5, 2015, the disclosure of which is incorporated by reference herein; U.S. Pub. No. 2011/0015660, entitled "Rotating Transducer Mount for Ultrasonic Surgical Instruments," published Jan. 20, 2011, now U.S. Pat. No. 8,461,744, issued June 11, 2013, the disclosure of which is incorporated by reference herein; and/or U.S. Provisional Application Ser. No. 61/410,603, filed Nov. 5, 2010, entitled "Energy-Based Surgical Instruments," the disclosure of which is incorporated by reference herein.

Of course, housing (130) and medical device (100) may include other configurations. For instance, housing (130) and/or medical device (100) may include a tissue cutting element and one or more elements that transmit bipolar RF energy to tissue (e.g., to coagulate or seal the tissue). An example of such a device is the ENSEAL® Tissue Sealing Device by Ethicon Endo-Surgery, Inc., of Cincinnati, Ohio.

Further examples of such devices and related concepts are disclosed in U.S. Pat. No. 6,500,176 entitled "Electrosurgical Systems and Techniques for Sealing Tissue," issued Dec. 31, 2002, the disclosure of which is incorporated by reference herein; U.S. Pat. No. 7,112,201, entitled "Electrosurgical Instrument and Method of Use," issued Sep. 26, 2006, the disclosure of which is incorporated by reference herein; U.S. Pat. No. 7,125,409, entitled "Electrosurgical Working End for Controlled Energy Delivery," issued Oct. 24, 2006, the disclosure of which is incorporated by reference herein; U.S. Pat. No. 7,169,146 entitled "Electrosurgical Probe and Method of Use," issued Jan. 30, 2007, the disclosure of which is incorporated by reference herein; U.S. Pat. No. 7,186,253, entitled "Electrosurgical Jaw Structure for Controlled Energy Delivery," issued Mar. 6, 2007, the disclosure of which is incorporated by reference herein; U.S. Pat. No. 7,189,233, entitled "Electrosurgical Instrument," issued Mar. 13, 2007, the disclosure of which is incorporated by reference herein; U.S. Pat. No. 7,220,951, entitled "Surgical Sealing Surfaces and Methods of Use," issued May 22, 2007, the disclosure of which is incorporated by reference herein; U.S. Pat. No. 7,309,849, entitled "Polymer Compositions Exhibiting a PTC Property and Methods of Fabrication," issued Dec. 18, 2007, the disclosure of which is incorporated by reference herein; U.S. Pat. No. 7,311,709, entitled "Electrosurgical Instrument and Method of Use," issued Dec. 25, 2007, the disclosure of which is incorporated by reference herein; U.S. Pat. No. 7,354,440, entitled "Electrosurgical Instrument and Method of Use," issued Apr. 8, 2008, the disclosure of which is incorporated by reference herein; U.S. Pat. No. 7,381,209, entitled "Electrosurgical Instrument," issued Jun. 3, 2008, the disclosure of which is incorporated by reference herein; U.S. Pub. No. 2011/0087218, entitled "Surgical Instrument Comprising First and Second Drive Systems Actuatable by a Common Trigger Mechanism," published Apr. 14, 2011, now U.S. Pat. No. 8,939,974, issued Jan. 27, 2015, the disclosure of which is incorporated by reference herein; and U.S. patent application Ser. No. 13/151,481, entitled "Motor Driven Electrosurgical Device with Mechanical and Electrical Feedback," filed Jun. 2, 2011, published as U.S. Pub. No. 2012/0116379 on May 10, 2012, now U.S. Pat. No. 9,161,803, issued Oct. 20, 2015, disclosure of which is incorporated by reference herein.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

II. Exemplary Visual Indicators on Ultrasonic Surgical Instrument

Examples described below relate to uses of exemplary visual indicators on various surgical instruments, including but not limited to ultrasonic surgical instruments and electrosurgical devices. It should be understood that any of the instruments or devices (10, 100) referred to above and/or described in any of the references cited herein may readily incorporate any of the teachings below. Various suitable ways in which such teachings may be combined will be apparent to those of ordinary skill in the art. As will be described in greater detail below, visual indicators may be used to provide visual feedback regarding operating parameters, etc., of a surgical instrument. Throughout this disclosure, reference numbers utilized with different alphanumeric extensions indicate similar components in different versions of a described reference (i.e., surgical instruments (50, 50A)).

Figure 3:
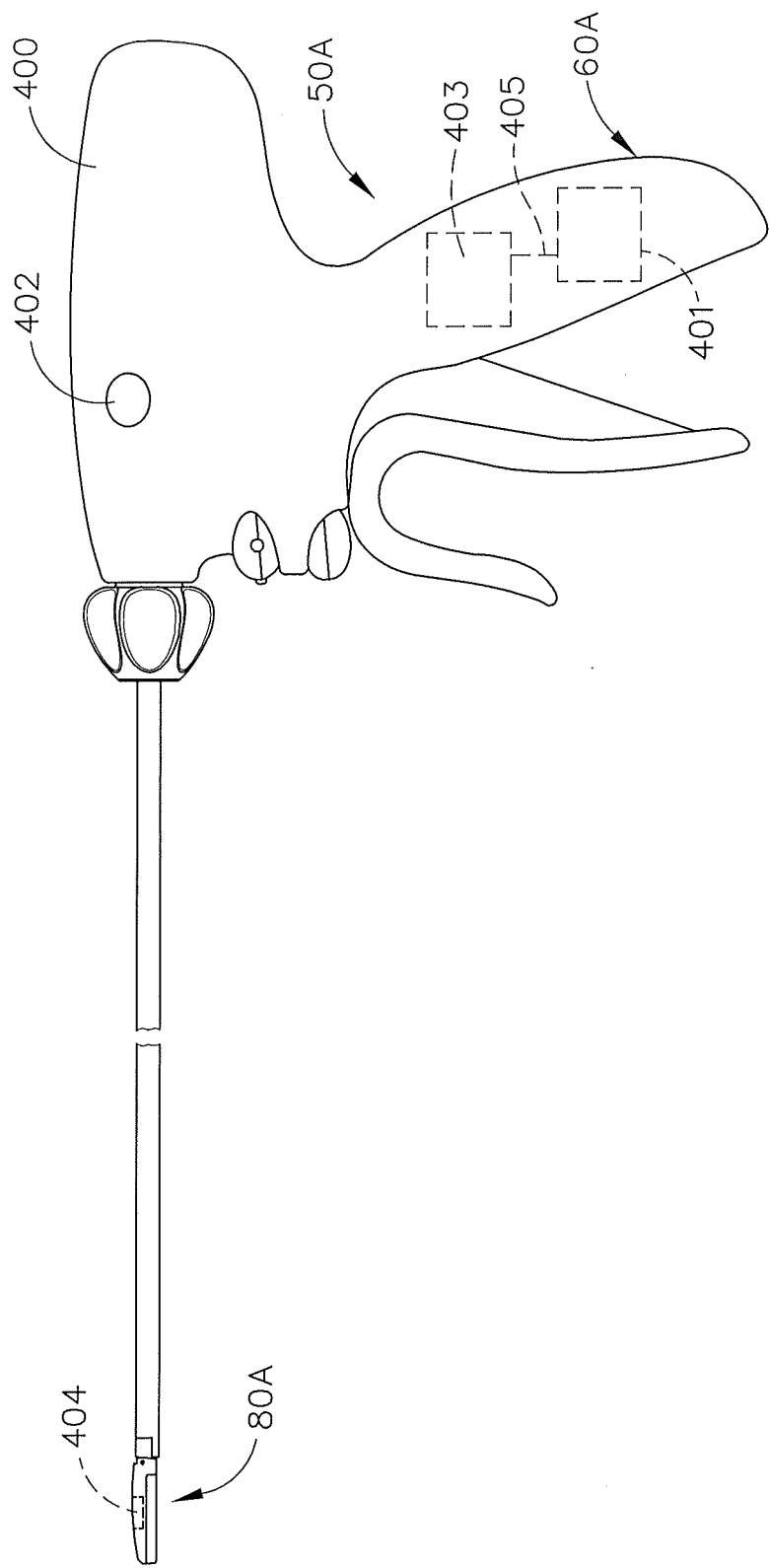
FIG. 3 depicts a side elevational view of an exemplary surgical instrument including a visual indicator.

FIG. 3 shows exemplary instrument (50A) that is a variation of instrument (10, 100) described above. Upper surface (400) of multi-piece handle assembly (60A) includes lighting display (402). End effector (80A) of surgical instrument (50A) may additionally or alternatively include light display (404). Light displays (402, 404) may comprise light-emitting diodes ("LEDs"). Instrument (50A) includes power source (401), control module (403), and electrical connection (405), each respectively similar to power source (110), control module (120), and electrical connection (150) of instrument (100) described above. Power source (401) may comprise, for example, a battery. Alternatively, instrument (50A) may be powered by an external power source, such as the power source described in U.S. Pub. No. 2011/0087212, now U.S. Pat. No. 8,986,302, issued Mar. 24, 2015. Control module (403) may, for example, read information from sensors, process the sensor data to drive light display (404), and process the sensor data to control an actuation and clamping of end effector (80A).

Figure 4:
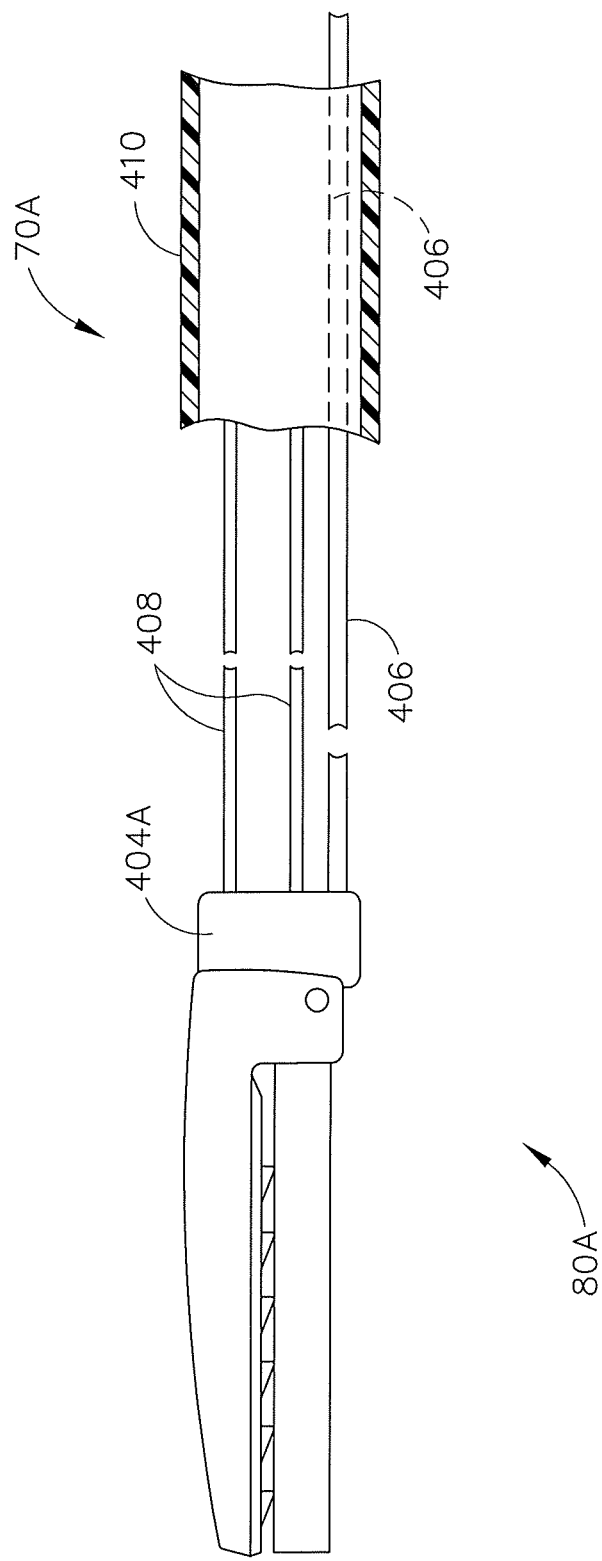
FIG. 4 depicts a partial side elevational view of a version of the end effector of FIG. 3 including an illuminating ring.
Figure 5:
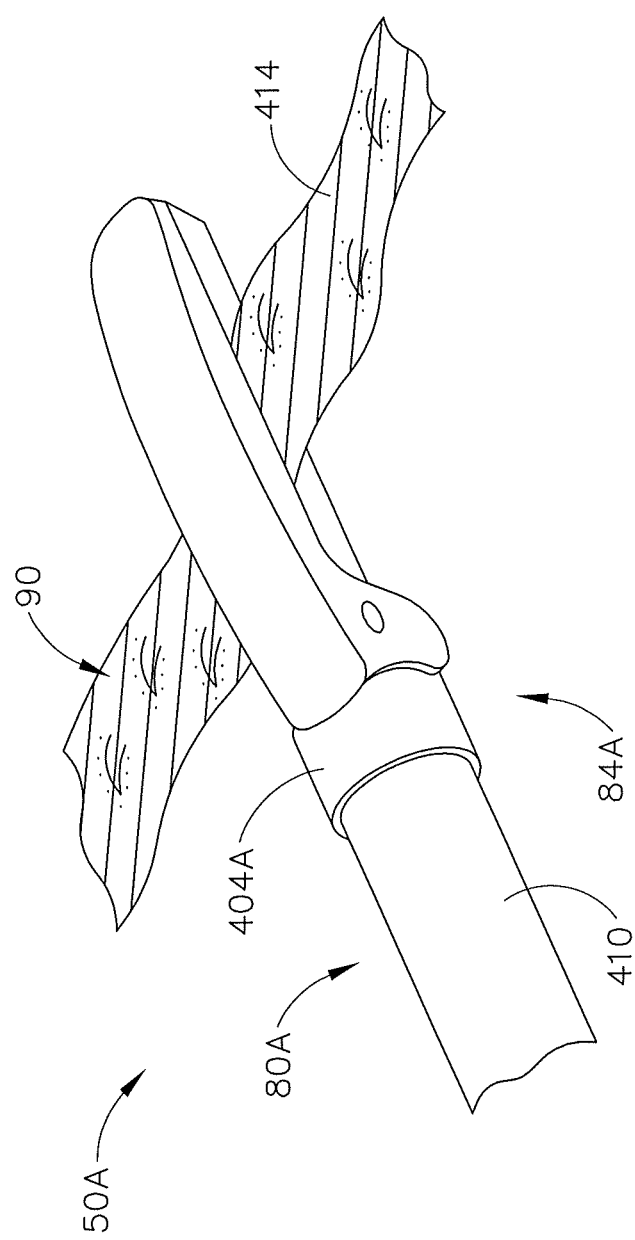
FIG. 5 depicts a fragmentary, perspective view of the end effector of FIG. 4.

FIGS. 4-5 show a version of end effector (80A) including light display (404) as illuminated ring (404A) disposed at a proximal end of end effector (80A). As shown in FIG. 5, ring (404A) may comprise at least one LED placed in clamp arm (84A) of end effector (80A). Referring back to FIG. 4, fiber optic cable (406) connects illuminated ring (404A) to a source (not shown) within instrument (50A), such as an electronics and/or battery cartridge housed within multi-piece handle assembly (60A). Mechanical connections (408) to end effector (80A) are disposed through a central aperture defined in illuminated ring (404A). Fiber optic cable (406) connects directly to illuminated ring (404A). Fiber optic cable (406) may carry light down shaft (410) of transmission assembly (70A) and through a lens on end effector (80A) to emit the light. Such light may present feedback to a surgeon that may be seen on a surgical monitor, preventing the need for the surgeon to look away from the surgical monitor or to listen for specific auditory tones providing information during surgery.

Figure 6:
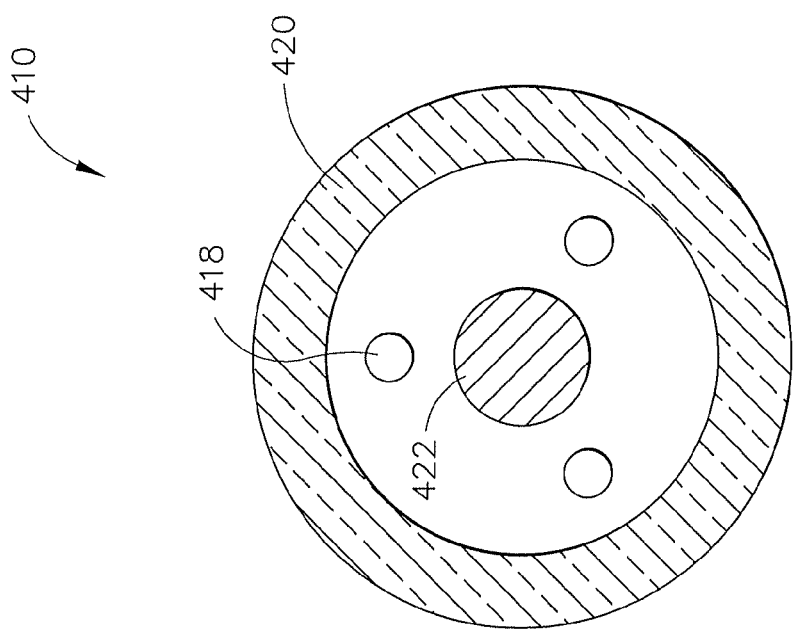
FIG. 6 depicts a cross-sectional end view of an exemplary end effector including a clear plastic lens and one or more LEDs disposed below the clear plastic lens and about internal components of the end effector.

The one or more LEDs used for light display (402) and/or light display (404, 404A) may include a single multicolor LED or a multiple of LEDs in varying colors. In use, fiber optic cable (406) transmits light down shaft (410) to end effector (80A), as described above. Additionally, the entire shaft (410) may comprise a transparent tube able to emit light from an LED housed within multi-piece handle assembly (60A). Referring to FIG. 6, clear lens (420) may be included as part of shaft (410) of end effector (80A). At least one LED (418) may be positioned under lens (420) and outside of internal device components (422) to transmit light through lens (420) that is not substantially interrupted and is visible to an operating surgeon using instrument (50A). Lens (420) may additionally comprise a frosted finish or any other suitable finish to diffuse the emitted light and make lens (420) appear to glow. End effector (80A) may include an incorporated lens to emit the received light, which may be used to signal various conditions or information to the surgeon using surgical instrument (50A).

Such information may include, among other things, an indication of the status of surgical instrument (50A), such as indications of cycle completion, an indication of power activation or deactivation, an indication of an approaching overload of instrument (50A), an indication of battery power, an indication of a need for an such, as for an improperly working instrument (50A), the temperature of end effector (80A), the application of energy, and/or the sealing status of tissue being operated upon by instrument (50A). For example, the light may turn red to indicate a heated end effector (80A) and blue to indicate a cool end effector (80A). Or, a pulsation of the light may signal when energy is being applied through end effector (80A) while a solid light may indicate energy is no longer being applied through end effector (80A). Additionally or alternatively, a yellow light may signal a caution or warning that instrument (50A), including but not limited to warnings that instrument (50A) is not properly working, is not ready to seal tissue, or itself was not used properly by the operating surgeon.

Adequate brightness of any of light displays (402, 404, 404A) may allow an operating surgeon and user of instrument (50A) to detect a changing color emitted by the respective light display in the user's vision. Light may be emitted, for example, as a glow that progressively changes from yellow to orange to red to communicate an increasing heat of a blade when in use, for example. Or an LED may glow and emit a different color to communicate that an overload is being approached as too much pressure is being applied upon tissue. Additionally or alternatively, shaft (410) may be printed or labeled with an organic LED ("OLED"); in which an emissive electroluminescent layer of an LED is a film of organic compounds that emit light responsive to an electric current, to eliminate the need to transmit light down shaft (410). Instead, an electrical connection may supply power necessary to illuminate the OLED material on shaft (410).

Referring back to FIG. 13, ring (404A) provides visual feedback to a surgeon using instrument (50A) in a procedure that tissue vessel (414) being operated upon which has been severed is in the process of being sealed or has a completed seal. For example, ring (404A) may flash when the sealing process starts and may become solid when the sealing status of vessel (414) of tissue (90), as described above, is complete. In use, when power is activated for instrument (50A), ring (404A) may turn on and blink with a light. Once a predetermined amount of time passes, the light from ring (404A) may stop blinking and become solid to indicate completion of the seal on vessel (414), as described above. Ring (404A) may use either a time algorithm to determine when to emit a solid light indicating sealing completion. Alternatively, ring (404A) may utilize a generator algorithm based on impedance to determine when to emit the solid light.

By emitting such light through ring (404A) or through a light pipe on end effector (80A), a surgeon may have visibility of that status of the sealing of vessel (414) at varying orientations of end effector (80A). Combining this effector with an audible change tone based on a generator algorithm indicated completion of a seal, multiple levels of feedback may be provided to a surgeon to indicate completion of the seal.

Figure 7:
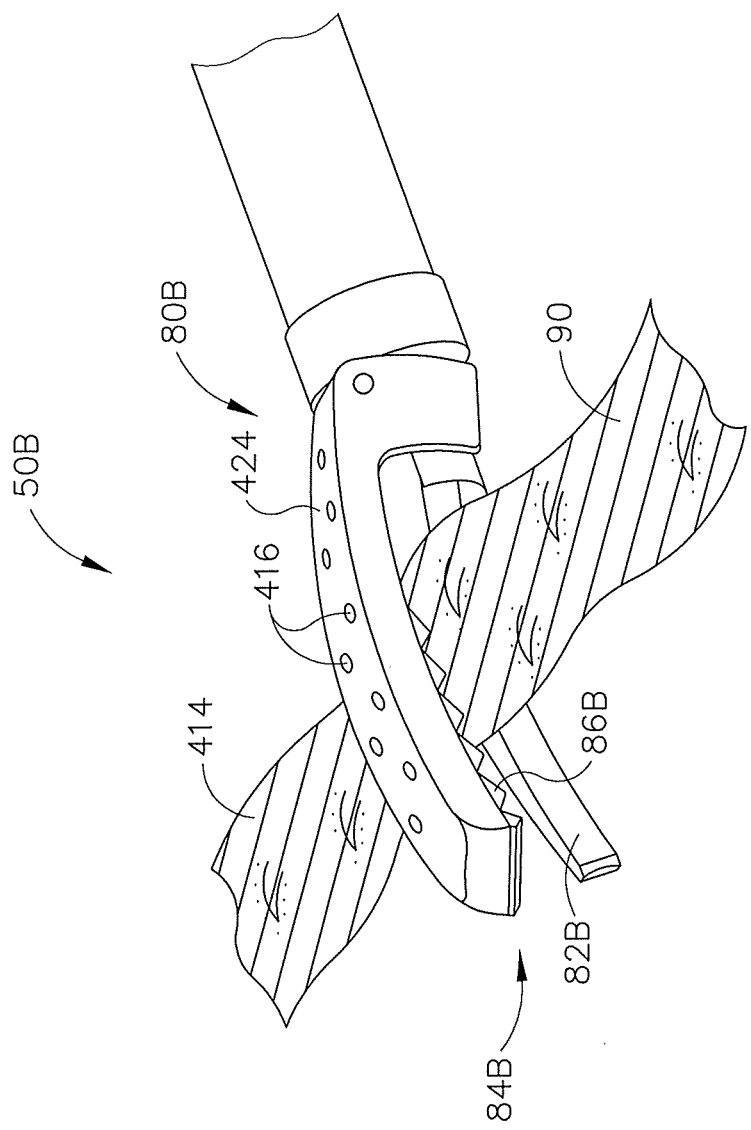
FIG. 7 depicts a perspective view of an exemplary alternative end effector shown to be operating on a tissue vessel, the end effector including a series of light-emitting dot structures on a top surface of an upper clamp arm while an attached clamp pad grips the vessel.

FIG. 7 shows exemplary instrument (50B) that is a variation of instrument (10, 100, 50A) described above. Instrument (50B) includes an end effector (80B) having a clamp arm (84B). Clamp arm (84B) includes small holes (416) allowing light from at least one LED, such as LED (418) of FIG. 6, to pass through. In use during a laparoscopic procedure, for example, light passing through holes (416) may be easily visible to an operating surgeon using instrument (50B) and would allow various types of information, as described above, to be communicated to the surgeon during the procedure.

Figure 8:
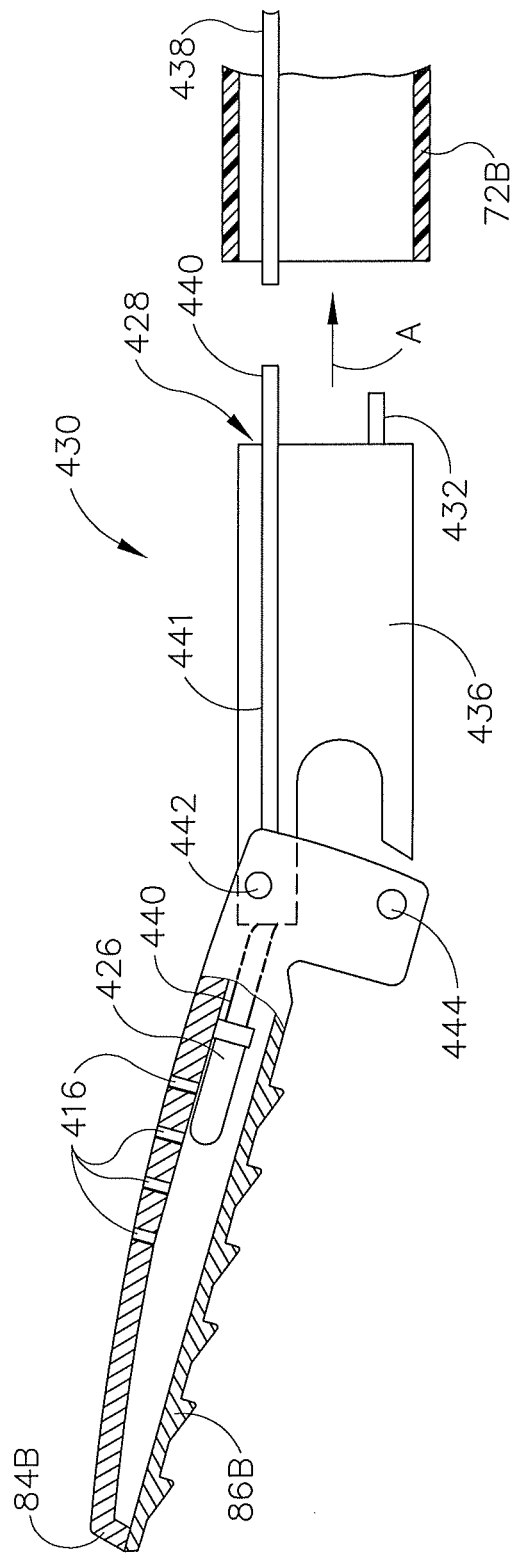
FIG. 8 depicts a cross-sectional side view of the end effector of FIG. 7.

Small holes (416) on top surface (424) of end effector (80B) may glow in various colors to emit light from end effector (80B) indicating certain information. End effector (80B) may include a molded interconnect device as described below and an illuminated clamp pad (86B). FIG. 8 shows tri-color LED (426) disposed in a cavity between upper clamp arm (84C) and clamp pad (86C) of end effector (80C). Light from LED (426) may glow and/or morph into various colors, and the light from LED (426) may be communicated and emitted through clamp pad (86B) and through holes (416) of clamp arm (84C) via one or more light pipe structures. Light may emit from two or more holes (416) simultaneously and/or at different times. With light emitting from holes (416) at different times, different sequences of emitted light may indicate different information. A light display emitted via holes (416) in a certain sequence may indicate information about the sealing process of tissue (90) as effected by end effector (80B). For example, a pair of rear lights of holes (416) may illuminate during a beginning time of the sealing processes. As the sealing progresses, more lights may begin to illuminate in a distal direction. The eventual illumination of all holes (416), including the pair of rear lights as well as a pair of front lights and those lights disposed therebetween that together comprise holes (416), may indicate a completed sealing of tissue (90) by end effector (80B).

Figure 9:
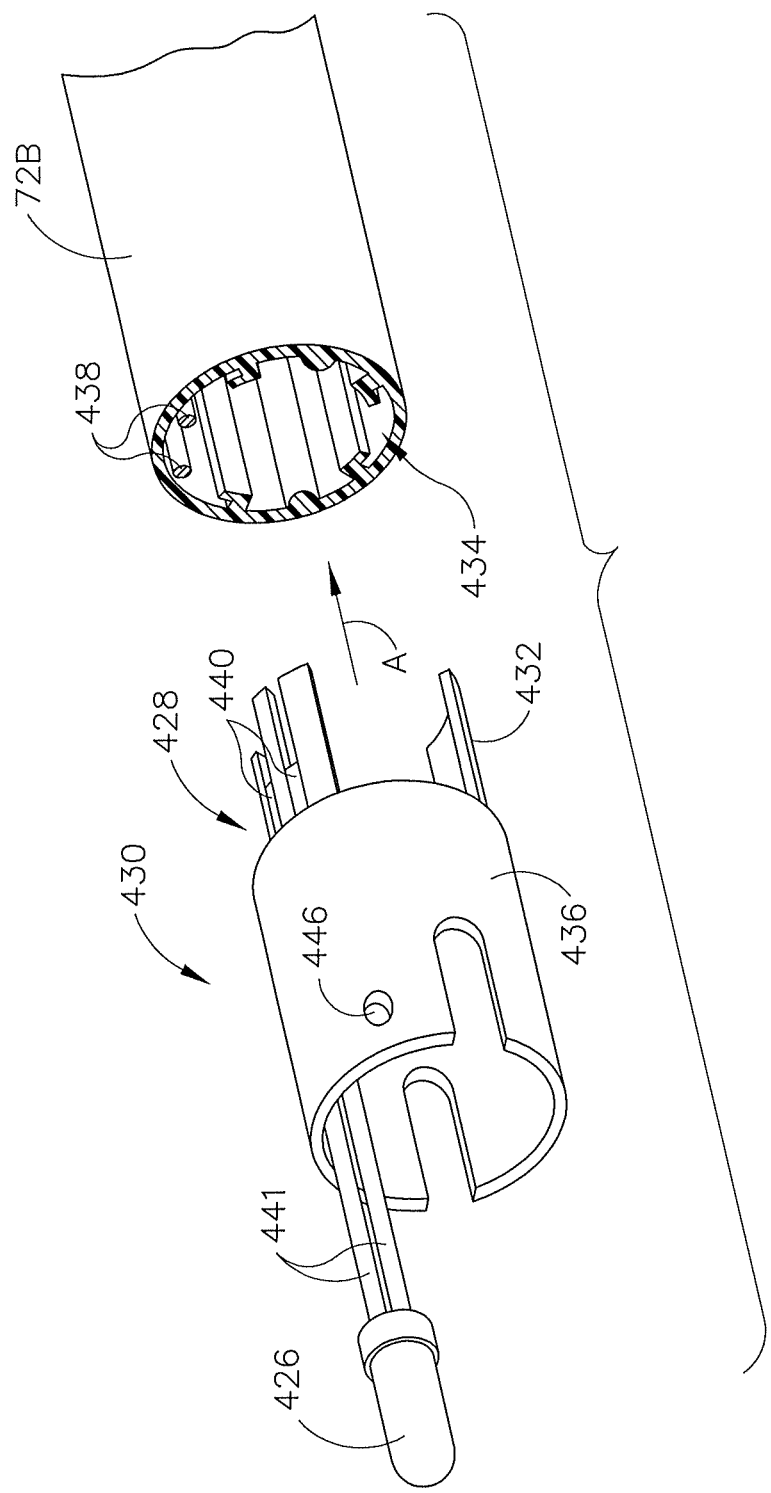
FIG. 9 depicts a perspective view of the exemplary end effector of FIG. 7 with the clamp arm and clamp pad removed.

Proximal end (428) of distal assembly (430) of end effector (80B) may snap into extruded outer tube or sheath (72B), described below, in the direction of arrow (A), as shown in FIGS. 8 and 9. One or more protrusions (432) extending from proximal end (428) of distal assembly (430) may snap into one or more notches (434) in outer sheath (72B). In the present example, distal assembly (430) includes an injection molded distal outer tube (436) from which protrusions (432) extend. Outer sheath (72B) is extruded and includes two electrical conduits (438) running through and within a length of outer sheath (72B). Outer tube (436) includes electrical conduits (440) that mate with electrical conduits (438) when outer tube (436) is coupled with extruded outer sheath (72B), such that electrical and mechanical connections are achieved simultaneously. A similar connection may be made for sheaths of ultrasonic instruments that comprise light pipes, as described in greater detail below. For example, a light connection is made similar to the manner the electrical connection is described above in the sense that a conduit such as a fiber optic cable may connect an internal LED to a light pipe sheath.

Conduits (440) are in electrical communication with LED (426) within clamp arm (84B) via wires (441) positioned between clamp pad (86C) and clamp arm (84B). Electrical conduits (440), wires (441), and conduits (438) together provide a signal from instrument (50B) to light LED (426). Light emitted from LED (426) illuminates semi-translucent clamp pad (86B) and shines through small holes (416) of clamp arm (84B), as described above.

Figure 10:
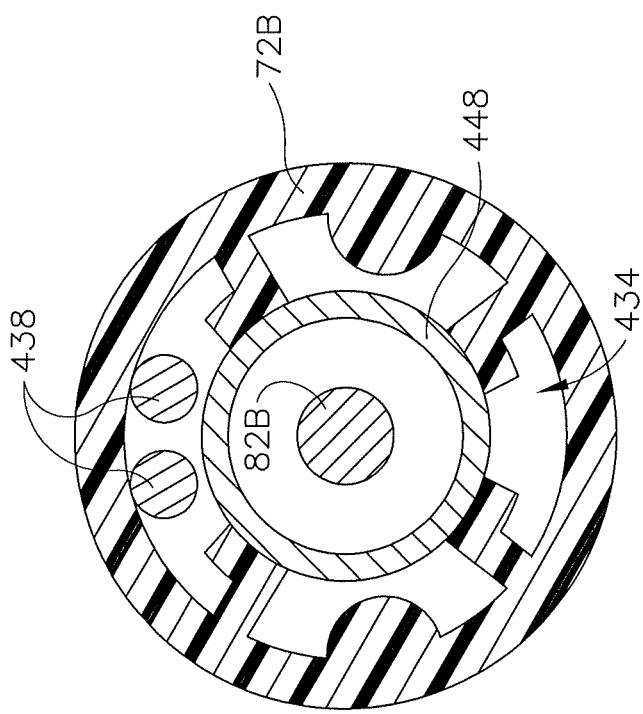
FIG. 10 depicts a cross-sectional view of the extruded outer sheath of FIG. 8.

Referring to FIG. 8, clamp arm (84B) may pivot with respect to outer tube (436) via pin (442) and be connected to a lower clamp arm via pin (444), similar to a manner described above for instrument (50). FIG. 9 shows distal assembly (430) without clamp arm (84B) and clamp pad (86B) attached. Aperture (446) is disposed in outer tube (436) and is configured to receive pivot pin (442) of clamp arm (84B). FIG. 10 shows a cross-sectional view of extruded outer sheath (72B) housing an inner tubular actuating member (448) and a harmonic blade (82B). Inner tubular actuating member (448) is translatable within outer sheath (72B) to selectively pivot clamp arm (84B) toward and away from blade (82B), as described above in various references cited herein. Blade (82B) is selectively activated with ultrasonic energy, as described in various references cited herein. Two electrical leads or electrical conduits (438) are molded within outer sheath (72B). The molded interconnect device design on extruded outer sheath (72B) thus contains electrical leads or conduits (438) that connect to distal assembly (430) as described above to power LED (426) inside clamp arm (84B), allowing a glow to be emitted in different colors to provide visual feedback to a user such as a surgeon. The glow may be a progressive change of color and/or an emission of different colors as described above.

Figure 11:
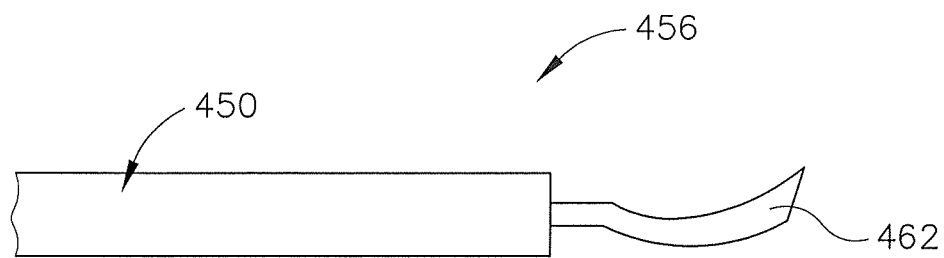
FIG. 11 depicts a side elevational view of an exemplary harmonic blade with an outer sheath capable of transmitting light along an entire length.
Figure 12:
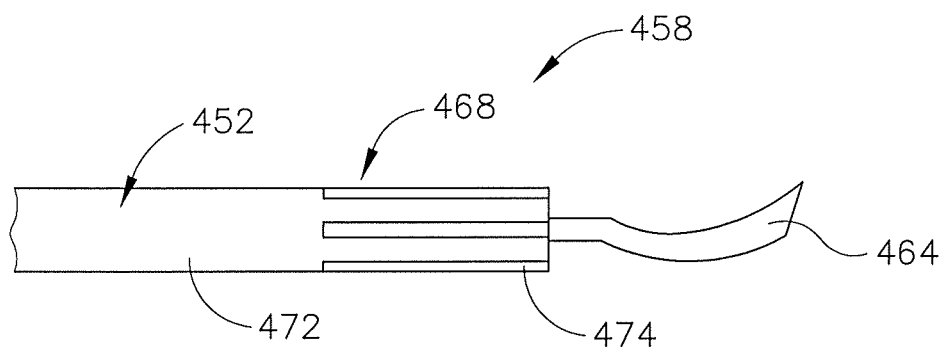
FIG. 12 depicts a side elevational view of an exemplary harmonic blade with an outer sheath including elongate localized areas capable of transmitting light from an internal LED source.
Figure 13:
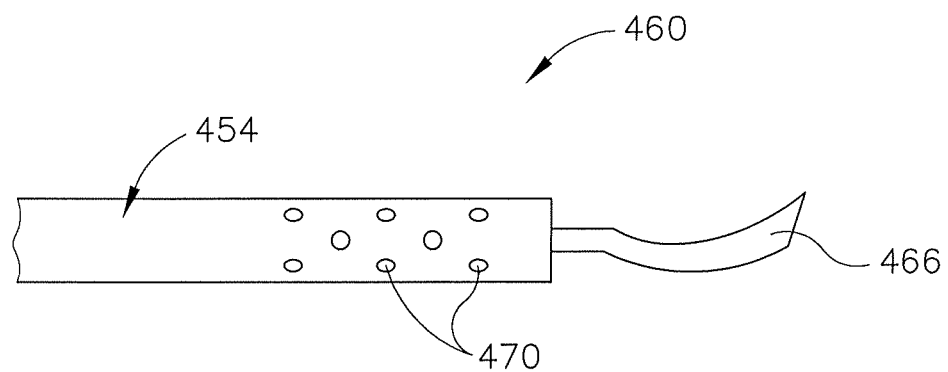
FIG. 13 depicts a side elevational view of an exemplary harmonic blade with an outer sheath including localized dot areas capable of transmitting light from an internal LED source.

FIGS. 11-13 show three different versions of respective sheaths (450, 452, 454) of ultrasonic surgical instruments (456, 458, 460) including harmonic blades (462, 464, 466). Ultrasonic surgical instruments (456, 458, 460) may be alternate versions of surgical instrument (50) or device (310) or other surgeon training tools. FIG. 11 shows a version in which the entire sheath (450) is a frosted clear material or light pipe communicating light from an internal LED, such as LED (418) described above, to a user of device (456). FIGS. 12 and 13 show two other versions of sheaths (452, 454) wherein selective areas of respective sheaths (452, 454) do not transmit light from LED (418), for example. FIG. 12 includes elongate localized areas (468) on sheath (452) that are light piped. Sheath (452) may include two portions, solid opaque tube (472) and light pipe tube (474) within outer solid opaque tube (472) that only shows through outer tube (472) in localized areas (468). FIG. 13 shows areas of sheath (454) including dots (470) that are light piped. For example, sheath (454) may comprise a clear material that is coated with an opaque coating and only emits light in localized areas, such as those defined by dots (470).

By viewing sheaths (450, 452, 454) of respective devices (456, 458, 460) during use, users of such devices may be provided with a visible indication of information such as how much force is being applied to respective blades (462, 464, 466). Force may either be measured by an increase in impedance on a respective blade (462, 464, 466) or by using bend sensors housed within a respective device shroud to determine how much force is being applied to a respective blade sheath assembly. Such devices could thus be used to assist with training surgeons on proper amounts of force to be used and technique necessary to optimize tissue effects during surgical operations such as laparoscopic tissue operations to sever tissue as described herein and as described in various references cited herein. Thus, when force is being applied to a respective blade (462, 464, 466) against tissue, and the force begins to increase, the respective lighted sheath may change color from green to yellow to orange and finally to red, for example, to indicate a final point for either hitting a solid tone, indicating too much force is being applied by a user via respective blade (462, 464, 466), or being submitted an error code. When using respective device (456, 458, 460), a user such as a surgeon may understand that a green or yellow sheath implies the surgeon is applying a correct amount of force against tissue and an orange or red sheath implies the application of too much force against tissue.

It should be understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Versions of the devices described above may have application in conventional medical treatments and procedures conducted by a medical professional, as well as application in robotic-assisted medical treatments and procedures.

Versions of described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various versions in the present disclosure, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical instrument comprising:
   (a) a body;
   (b) a transmission assembly extending distally from the body;
   (c) an end effector at a distal end of the transmission assembly, wherein the end effector is operable to deliver ultrasonic energy from the transmission assembly to a surgical site; and
   (d) a visual indicator disposed within the transmission assembly or the end effector, wherein the transmission assembly or the end effector comprises at least one light emitting feature formed in the transmission assembly or the end effector, wherein the at least one light emitting feature is configured to emit light produced by the visual indicator from within the transmission assembly or the end effector to an exterior of the transmission assembly or the end effector, wherein the visual indicator is operable to visually indicate an operating parameter associated with the end effector via the at least one light emitting feature;
   wherein the end effector comprises an upper clamp arm, wherein the visual indicator comprises one or more LEDs, wherein the at least one light transmitting feature comprises a series of holes formed in the upper clamp arm configured to transmit light from the one or more LEDs.

2. The surgical instrument of claim 1, further comprising a lighting device disposed on the body.

3. The surgical instrument of claim 1, wherein the visual indicator further comprises a lighting device disposed on the end effector.

4. The surgical instrument of claim 1, wherein the at least one light transmitting feature comprises a clear lens, wherein the visual indicator comprises one or more LEDs disposed below the clear lens.

5. The surgical instrument of claim 1, wherein the end effector further comprises a lower clamp pad attached to the upper clamp arm, wherein the one or more LEDs are disposed between the upper clamp arm and the lower clamp pad.

6. The surgical instrument of claim 5, wherein the end effector further comprises a distal assembly and an extruded outer sheath, wherein a first set of electrical conduits extend from the one or more LEDs through the distal assembly, wherein the distal assembly is configured to be removably attached to a proximal end of the extruded outer sheath.

7. The surgical instrument of claim 6, wherein the extruded outer sheath is injection molded and comprises a second set of electrical conduits, wherein the second set of electrical conduits is configured for an electrical connection to the first set of electrical conduits when the distal assembly is attached to the extruded outer sheath.

8. The surgical instrument of claim 6, wherein the distal assembly includes one or more of one of protrusions or notches configured to be received in one or more of the other of protrusions or notches disposed in the extruded outer sheath.

9. The surgical instrument of claim 6, wherein the distal assembly is configured to be removably attached to the proximal end of the extruded outer sheath in a snap-fit connection.

10. The surgical instrument of claim 6, wherein the distal assembly comprises a molded distal outer tube, wherein the upper clamp arm is pivotally connected to the molded distal outer tube.

11. The surgical instrument of claim 1, wherein the one or more LEDs emit a glow configured to be emitted in at least one of a series of colors.

12. The surgical instrument of claim 11, wherein each color is associated with a temperature level of a blade of the end effector.

13. An ultrasonic surgical instrument comprising:
   (a) a sheath;
   (b) an ultrasonic blade extending from the sheath; and
   (c) a light source housed in the ultrasonic surgical instrument, wherein the light source is configured to emit light in response to forces exerted at the ultrasonic blade;

wherein the sheath comprises light-transmitting portions configured to transmit light from the light source;

wherein the sheath comprises a solid opaque tube and a light pipe tube disposed within the solid opaque tube, and the solid opaque tube comprises elongate localized areas, and wherein light from the light source and light pipe tube are transmitted only through the elongate localized areas.

14. The instrument of claim 13, wherein the localized areas comprise a series of dots.

15. An ultrasonic surgical instrument comprising:
(a) a sheath;
(b) an ultrasonic blade extending from the sheath; and
(c) a light source housed in the ultrasonic surgical instrument, wherein the light source is configured to emit light in response to forces exerted at the ultrasonic blade;

wherein the sheath comprises light-transmitting portions configured to transmit light from the light source;

wherein the sheath comprises a series of dots comprising localized areas, and wherein the dots are light piped to transmit light from the light source only through the localized areas.

* * * * *